(12) United States Patent
Zhang et al.

(10) Patent No.: US 9,896,474 B2
(45) Date of Patent: Feb. 20, 2018

(54) (3A,9B,10A,13A,14B,17A,20S,22E)-ERGOSTA-5,7,22-TRIEN-3-OL AND METHODS OF PREPARING AND USING THE SAME

(71) Applicant: Zhengyuantang (Tianjin Binhai New Area) Biotech Co., Ltd., Tianjin (CN)

(72) Inventors: Yaozhou Zhang, Tianjin (CN); Jiachen Sun, Tianjin (CN); Lei Jiang, Tianjin (CN); Jian Zhang, Tianjin (CN); Yujiao Chen, Tianjin (CN); Xiaoqian Zhang, Tianjin (CN); Simiao Du, Tianjin (CN); Pengai Gu, Tianjin (CN); Jinsong Cui, Tianjin (CN)

(73) Assignee: ZHENGYUANTANG (TIANJIN BINHAI NEW AREA) BIOTECH CO., LTD., Tianjin (CN)

( * ) Notice: Subject to any disclaimer, the term of this patent is extended or adjusted under 35 U.S.C. 154(b) by 0 days.

(21) Appl. No.: 15/227,936

(22) Filed: Aug. 3, 2016

(65) Prior Publication Data

US 2016/0340383 A1 Nov. 24, 2016

Related U.S. Application Data

(63) Continuation-in-part of application No. PCT/CN2014/081517, filed on Jul. 2, 2014.

(30) Foreign Application Priority Data

Jun. 4, 2014 (CN) .......................... 2014 1 0244394

(51) Int. Cl.
*C07J 15/00* (2006.01)

(52) U.S. Cl.
CPC ......... *C07J 15/005* (2013.01); *C07B 2200/13* (2013.01)

(58) Field of Classification Search
CPC ........................... C07J 15/005; C07B 2200/13
USPC ........................................................ 514/182
See application file for complete search history.

(56) References Cited

U.S. PATENT DOCUMENTS

2008/0249075 A1* 10/2008 Messinger ............. C07J 15/005
 514/172

* cited by examiner

*Primary Examiner* — Yong Chu
(74) *Attorney, Agent, or Firm* — Matthias Scholl P.C.; Matthias Scholl

(57) ABSTRACT

(3α,9β,10α,13α,14β,17α,20S,22E)-Ergosta-5,7,22-trien-3-ol. A method for preparing the same by drying a fruiting body of *Cordyceps militaris*, grinding the fruiting body to yield ultrafine powders; boiling and extracting the ultrafine powders, centrifuging and collecting a precipitate. A method for treating a tumor by administering to a patient in need of treating a tumor (3α,9β,10α,13α,14β,17α,20S,22E)-ergosta-5,7,22-trien-3-ol.

3 Claims, 17 Drawing Sheets

(3A,9B,10A,13A,14B,17A,20S,22E)-ERGOSTA-5,7,22-TRIEN-3-OL AND METHODS OF PREPARING AND USING THE SAME

CROSS-REFERENCE TO RELATED APPLICATIONS

This application is a continuation-in-part of International Patent Application No. PCT/CN2014/081517 with an international filing date of Jul. 2, 2014, designating the United States, now pending, and further claims priority benefits to Chinese Patent Application No. 201410244394.5 filed Jun. 4, 2014. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND OF THE INVENTION

Field of the Invention

The invention relates to (3α,9β,10α,13α,14β,17α,20S,22E)-ergosta-5,7,22-trien-3-ol and methods of preparing and using the same.

Description of the Related Art

Radiotherapy and chemotherapy are typically used methods to treat cancer. However, these two methods often cause various side effects, such as, bone marrow suppression, immune dysfunction, emotional imbalance, baldness, and drug resistance, to name a few.

SUMMARY OF THE INVENTION

In view of the above-described problems, it is one objective to develop antitumor drugs from natural plants based on the principles of Chinese traditional medicine that have fewer side-effects.

In particular, it is one objective of the invention to provide (3α,9β,10α,13α,14β,17α,20S,22E)-ergosta-5,7,22-trien-3-ol.

It is another objective of the invention to provide a method for preparing (3α,9β,10α,13α,14β,17α,20S,22E)-ergosta-5,7,22-trien-3-ol.

It is still another objective of the invention to provide a method for using (3α,9β,10α,13α,14β,17α,20S,22E)-ergosta-5,7,22-trien-3-ol.

To achieve the above objective, in accordance with one embodiment of the invention, there is provided (3α,9β,10α,13α,14β,17α,20S,22E)-ergosta-5,7,22-trien-3-ol, having a molecular formula of $C_{28}H_{44}O$, and a chemical structure represented by Formula (I).

Formula (I)

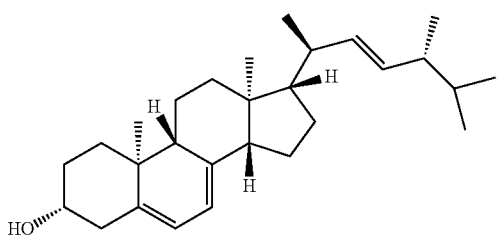

The CAS Registry Number of (3α,9β,10α,13α,14β,17α,20S,22E)-ergosta-5,7,22-trien-3-ol is 1654010-15-7.

This compound is also known by the following chemical name: (3R,9R,10S,13S,14S,17S)-17-(2S,5R,E)-5,6-dimethylhept-3-en-2-yl)-10,13-dimethyl-2,3,4,9,10,11,12,13,14,15,16,17-dodecahydro-1H-cyclopenta(α)phenanthren-3-ol).

As shown in Formula (II), the chiral carbons at C-3, C-9, C-10, and C-24 are in an R configuration, and the chiral carbons of C-13, C-14, C-17, and C-20 are in an S configuration.

Formula (II)

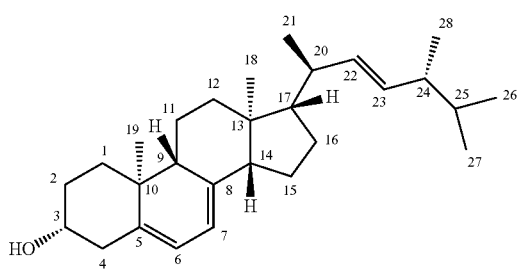

In a class of this embodiment, the compound is obtained from a fruiting body of Cordyceps militaris by grinding, extraction-concentration, and separation.

In accordance with one embodiment of the invention, there is provided a method for preparing the ergosterol compound, and the method comprises the following steps:
1) drying a fruiting body of Cordyceps militaris, and ultrafine grinding the fruiting body to yield ultrafine powders;
2) boiling and extracting the ultrafine powders, centrifuging and collecting a precipitate;
3) repeating 2) for between 1 and 5 times, digesting the precipitate obtained from 2) by an organic reagent being selected from the group consisting of acetone, ethanol, methanol, and a mixture thereof; collecting a first supernatant after the digesting, centrifuging, and collecting a second supernatant, concentrating and drying the second supernatant to yield a crude extract;
4) completely dissolving the crude extract obtained from 3) by a mobile phase, performing separation using a dynamic axial compression (DAC) normal-phase preparative liquid chromatography column, and eluting using binary mobile phases; wherein the mobile phase is a mobile phase A, a mobile phase B, or a combination thereof, and both the mobile phase A and the mobile phase B are selected from the group consisting of n-hexane, ethyl acetate, ethanol, dichloromethane, methanol, and a mixture thereof; the elution mode is gradient elution for 60 min, a detection wavelength is 260 nm, and an objective peak is collected and dried for yielding an intermediate component; and
5) completely dissolving the intermediate component obtained from 4) by a mobile phase, performing separation using the DAC normal-phase preparative liquid chromatography column, and eluting using the binary mobile phases; wherein the mobile phase is the mobile phase A, the mobile phase B, or the combination thereof, and both the mobile phase A and the mobile phase B are selected from the group consisting of n-hexane, ethyl acetate, ethanol, dichloromethane, methanol, and a mixture thereof; the elution mode is gradient elution for 180 min, the detection wavelength is 260 nm, an objective peak is collected and dried for yielding an objective single crystal.

In a class of this embodiment, the water boiling and extracting in 2) is conducted at a temperature of between 70 and 100° C. for between 1 and 2 hrs.

In a class of this embodiment, the precipitate in 3) and the organic reagent are mixed and digested according to a weight-to-volume ratio of 1 kg: (3-8 L).

In accordance with one embodiment of the invention, there is provided a crystal acquired by crystallization of the compound. A single crystal type of the crystal belongs to a monoclinic crystal system, crystal axes thereof are a=9.848(2), b=7.5529(15), and c=35.074(7). Angles between crystal faces are α=90°, β=95.62(3)°, and λ=90°.

In accordance with one embodiment of the invention, there is provided a method for preparing the crystal of the compound, the method comprising:

1) dissolving the ergosterol compound in a solvent with every 150 mg of the ergosterol compound corresponding to 3 mL of the solvent to yield a solution, allowing the solution to stand at a temperature of 16° C. for natural evaporation and crystallization, and collecting crystals when the solution is evaporated to ⅓ volume of an original volume; wherein the collected crystals are monoclinic crystals, and the solvent is selected from the group consisting of n-hexane, tetrahydrofuran, ethyl acetate, ethanol, methanol, and a mixture thereof; and 2) leaching the monoclinic crystals, and washing the monoclinic crystals with n-hexane at a temperature of −20° C.

In a class of this embodiment, a product obtained from 2) is directly analyzed by X-ray crystallography after the washing.

In accordance with one embodiment of the invention, there is provided a method for treating tumor comprising administering to a patient in need thereof the compound and/or the crystal of the compound and/or a pharmaceutical composition comprising the same.

In a class of this embodiment, the tumor is liver cancer, lung cancer, breast cancer, uterine cancer, or colon cancer.

In accordance with one embodiment of the invention, there is provided a pharmaceutical composition for treating tumor comprising: the compound and/or the crystal of the compound, and one or multiple pharmaceutically acceptable excipients.

The above pharmaceutically acceptable excipients can be any conventional excipients in the field of the pharmaceutical preparations. The selection of the specific excipient is dependent on the administration mode or the type and the state of the disease for specific patients. The preparation method of proper pharmaceutical composition for specific administration mode is well known by the persons skilled in the pharmaceutical art. For example, the pharmaceutically acceptable excipient comprises: diluents, carriers, fillers, binders, humectants, disintegrators, absorption accelerators, surfactants, lubricants and the like adsorption carrier that are conventional in the pharmaceutical art; and flavoring agents, preservatives and sweeteners can also be added into the pharmaceutical composition if necessary.

The above antitumor pharmaceutical composition can be prepared into tablets, capsules, powders, granules, pellets, solutions, suspensions, syrups, buccal tablets, sublingual tablets, injections, ointments, suppositories, inhalation agent multiple forms. Various forms of the drug can be prepared according to conventional methods in the field of pharmacy.

Advantages according to embodiments of the invention are summarized as follows:

The (3α,9β,10α,13α,14β,17α,20S,22E)-ergosta-5,7,22-trien-3-ol and/or the crystal of the ergosterol compound are new compounds isolated from fruiting bodies of *Cordyceps militaris*, purities thereof reaches 99 wt. %. The compound has stable quality, significant antitumor activity, simple preparation, good repeatability, high practicability, and is adaptable for large-scale industrial production.

BRIEF DESCRIPTION OF THE DRAWINGS

The invention is described hereinbelow with reference to the accompanying drawings, in which:

FIGS. 4A, 4B, 4C, and 4D are nuclear magnetic resonance (NMR) analysis charts of compound C310-6 in accordance with one embodiment of the invention, in which, FIG. 4A is a data map of 1D1HNMR spectrum (CDCl3, 600 MHz); FIG. 4B is a data map of 1D13CNMR spectrum (CDCl3, 150 MHz); FIG. 4C is a HMBC data map; and FIG. 4D is DEPT 135 data map;

DETAILED DESCRIPTION OF THE EMBODIMENTS

Figure 1:
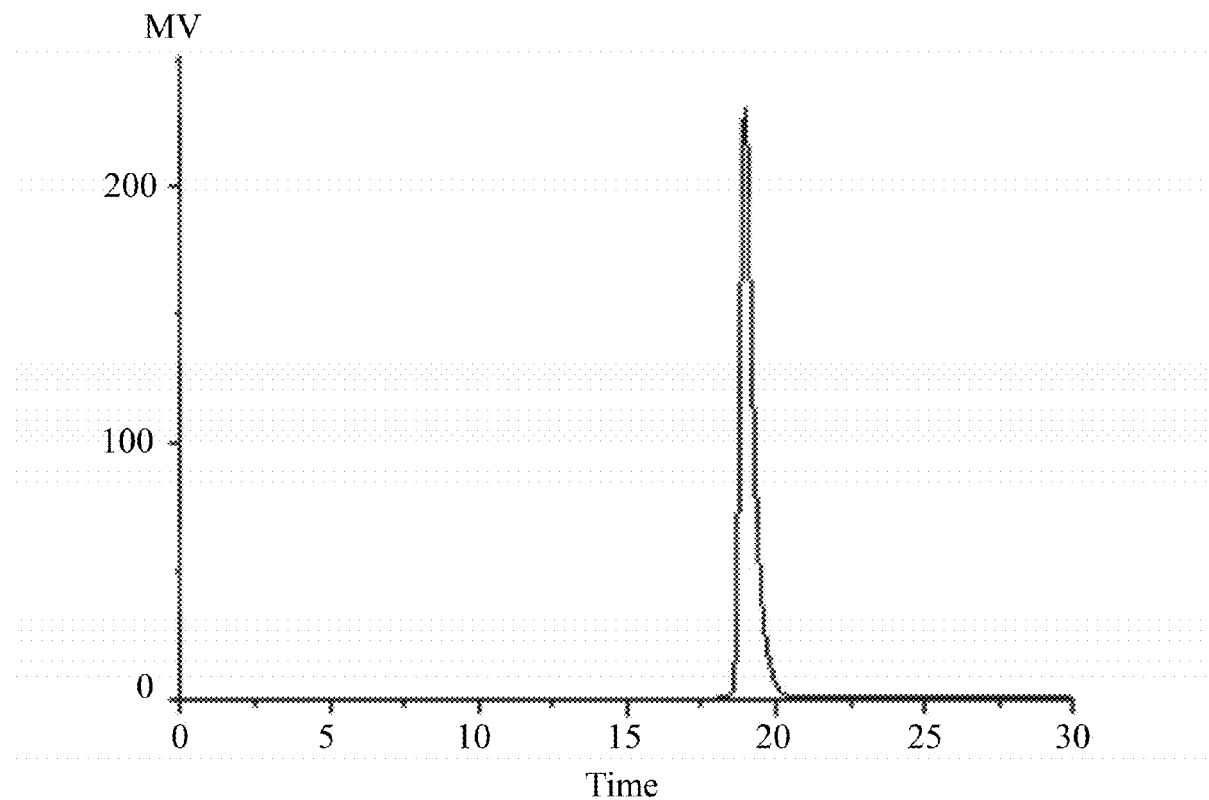
FIG. 1 is an HPLC analysis chart of compound C310-6 in accordance with one embodiment of the invention.

For further illustrating the invention, experiments detailing (3α,9β,10α,13α,14β,17α,20S,22E)-ergosta-5,7,22-trien-3-ol and methods of preparing and using the same are described below. It should be noted that the following examples are intended to describe and not to limit the invention.

Experiment materials adopted herein are as follows: fruiting bodies of *Cordyceps military* was purchased from Zhengyuantang (Tianjin) Biotechnology Co., Ltd; human hepatoma cells Hep-g2 was purchased from the American Type Culture collection (ATCC); human lung cancer cells A549 were purchased from ATCC; H22 hepatoma cell lines (4th generation) were purchased from China Center for Type Culture Collection (CCTCC); Lewis lung cancer cell lines (6th generation) were purchased from CCTCC; KM mice (18-22 g) (animal license number: SCXK (Beijing) 2012-0001, Certificate of Conformity: 11400700020779) were purchased from Beijing Vital River Laboratory Animal Technology Limited; and C57BL/6 mice (18-22 g) (animal license number: SCXK (Beijing) 2012-0001, Certificate of Conformity: 11400700020779) were purchased from Beijing Vital River Laboratory Animal Technology Co., Ltd.

Experiment reagents employed are as follows: preparative HPLC grade n-hexane, ethyl acetate, ethanol, methylene chloride, and methanol purchased from Tianjin Concord Technology Co., Ltd.; F-12K medium and MEM medium were purchased from Life Technologies Corporation; CTX tablets was purchased from Tianjin Jinshi Pharmaceutical Co., Ltd.; and Tween 80 was packed by Beijing Borunlaite science & technology Co., Ltd.

The experimental equipment employed is as follows: ultrafine grinding machine was purchased from Shandong Sanqing stainless steel equipment Co., Ltd.; Benchtop refrigerated centrifuge was purchased from Thermo Scientific company; Chinese medicine extraction tank with a capacity of 30 liters was purchased from Shanghai Shunyi Experiment Equipment Co., Ltd.; thermostat blast oven was purchased from Shanghai Yiheng Scientific Instrument Co., Ltd; rotary evaporator was purchased from Shanghai Yarong Biochemical instrument Factory; DAC 50 normal phase chromatography column and DAC 150 normal phase chromatography column were purchased from Jiangsu Hanbang Technology Co., Ltd.; Kromasil normal phase chromatography column (250 mm×4.6 mm, 5 μm, 100 Å) was purchased from Beijing Zhengxiang Industry and Trade Co., Ltd; iCELLigence real-time label-free cell function analyzer was purchased from ACEA BIO (Hangzhou) Co., Ltd.; Hitachi HPLC was purchased from Tianmei (China) Co., Scientific Instrument Co., Ltd.; and Single-crystal X-ray diffractometer is purchased from Rigaku Corporation Japan.

Example 1

Preparation of (3α,9β,10α,13α,14β,17α,20S,22E)-ergosta-5,7,22-trien-3-ol ("C310-6")

Preparation of Crude Extract of C310-6

1. Ultrafine Grinding

Dried fruiting bodies of *Cordyceps militaris* were provided as raw materials and placed in an ultrafine pulverizer to perform ultrafine grinding to yield ultrafine powders, during which a time for the ultrafine grinding was 20 min, and water at a temperature of 5° C. was employed as an internal cooling solution of the ultrafine pulverizer.

2. Water Boiling Extraction

The ultrafine powders was continuously performed with water boiling extraction for three times, each water boiling lasted for 70 min (during which, the water was heated to 100° C., and continued to heat for another 30 min after boiling the water for 40 min) And the process was specifically conducted as follows:

First water boiling: 3 kg of the ultrafine powders was added to 24 L of hyperpure water and fully stirred to make a resulting mixture uniform and excluded from obvious masses. Thereafter, a herb extraction tank having a capacity of 30 L was started, and water boiling was conducted for 70 min. A product was dispensed by centrifugal cups having a capacity of 1 L and balanced, and when the temperature was cooled to the room temperature of 25° C., the product was centrifuged at a rotational speed of 6000 rpm for 30 min. And thereafter, a precipitate was collected.

Second water boiling: the precipitate obtained from the first water boiling was added with 12 L of hyperpure water and fully stirred to make a resulting mixture uniform and excluded from masses. The herb extraction tank having the capacity of 30 L was started, and water boiling was conducted for 70 min. After the water boiling, a product was performed with the same treatment as the first water boiling process so as to collect a precipitate.

Third water boiling: the precipitate obtained from the second water boiling was added with 9 L of hyperpure water and fully stirred to make a resulting mixture uniform and excluded from masses. The herb extraction tank having the capacity of 30 L was started, and water boiling was conducted for 70 min. After the water boiling, a product was performed with the same treatment as the first water boiling process so as to collect a precipitate. The precipitate was transferred to an air dry oven at a constant temperature of 60° C., and then vacuum dried.

3. Organic Reagent Extraction

The precipitate after drying was ground by a pulverizer, and then added with an organic reagent according to a weight to volume ratio of 1:5. The organic reagent was a 50% acetone-ethanol solution. A resulting mixture was uniformly mixed, then sealed by a fresh keeping film for leaching for overnight. Thereafter, a first supernatant was collected. The first supernatant was centrifuged at a rotational speed of 6000 rpm for 30 min to yield a second supernatant. The second supernatant was then condensed in a rotary evaporator and transferred to the air dry oven at the constant temperature of 60° C., so as to obtain the crude extract of C310-6.

Preparation of Intermediate C310-6

1. Experiment in DAC 50

Figure 18:
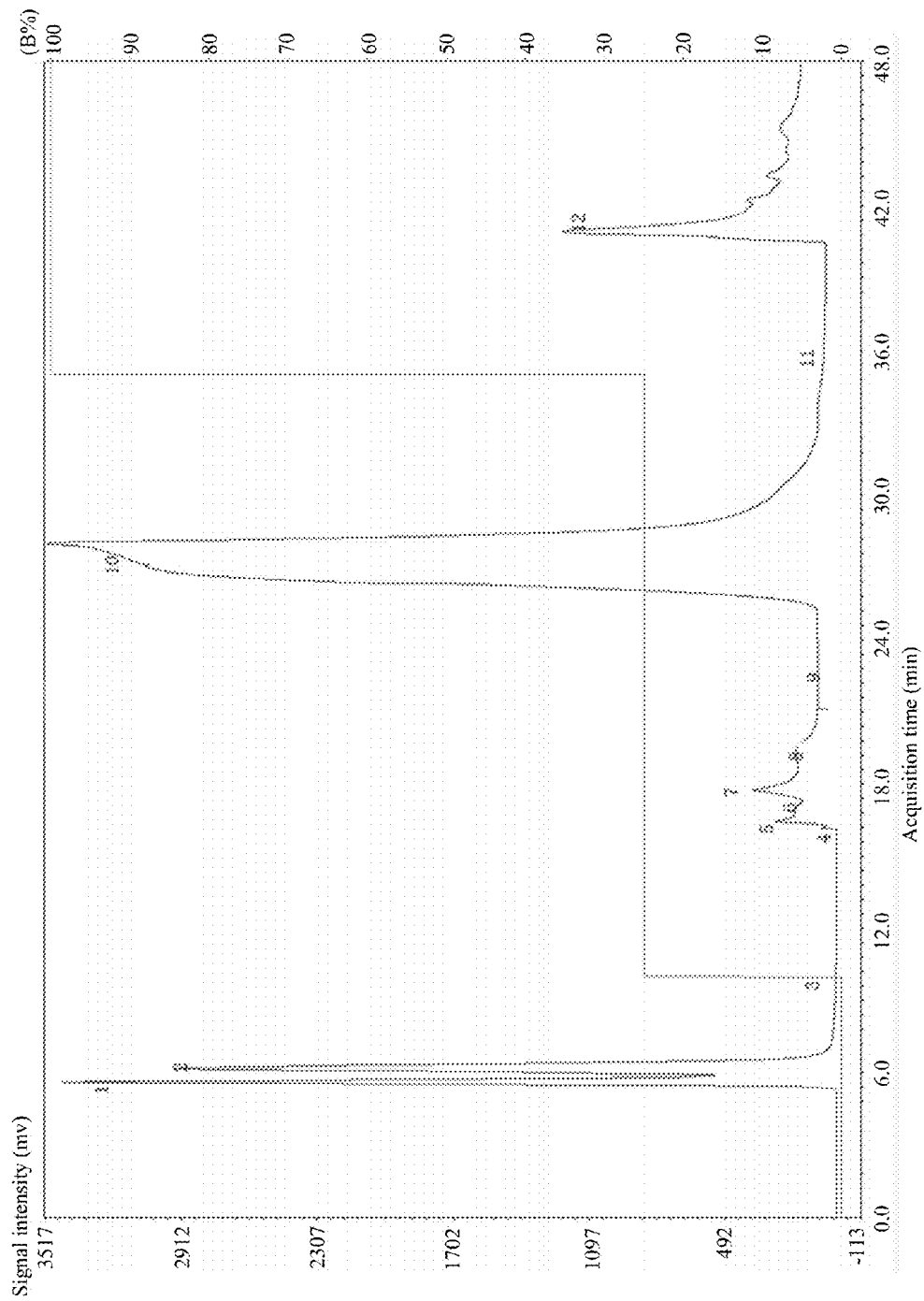
FIG. 18 is a DAC 50 normal-phase chromatography in accordance with one embodiment of the invention, in which, an abscissa represents an acquisition time (min), an ordinate represents a signal intensity (MV), a curve represents a chromatography curve, and a straight broken line represents a mixing concentration of a mobile phase.

The crude extract of C310-6 was completely dissolved in a mobile phase to prepare a solution having a concentration of 50 mg/mL. The solution was separated by a DAC 50 normal-phase preparative liquid chromatography column (250 mm×50 mm, 10 μm, 100 Å) with a detection wavelength of 260 nm, and then performed with elution separation using an A-B binary mobile phase system. The mobile phase A and the mobile phase B were n-hexane and ethyl acetate respectively. The gradient elution was employed for 60 min using 100% n-hexane and 100% ethyl acetate, and a flow rate was controlled at 80 mL/min, and an injection volume was 20 mL. The chromatogram was illustrated in FIG. 18. A tenth peak in FIG. 18 was collected and dried to acquire the intermediate component of C310-6.

2. Experiment in DAC 150

Figure 19:
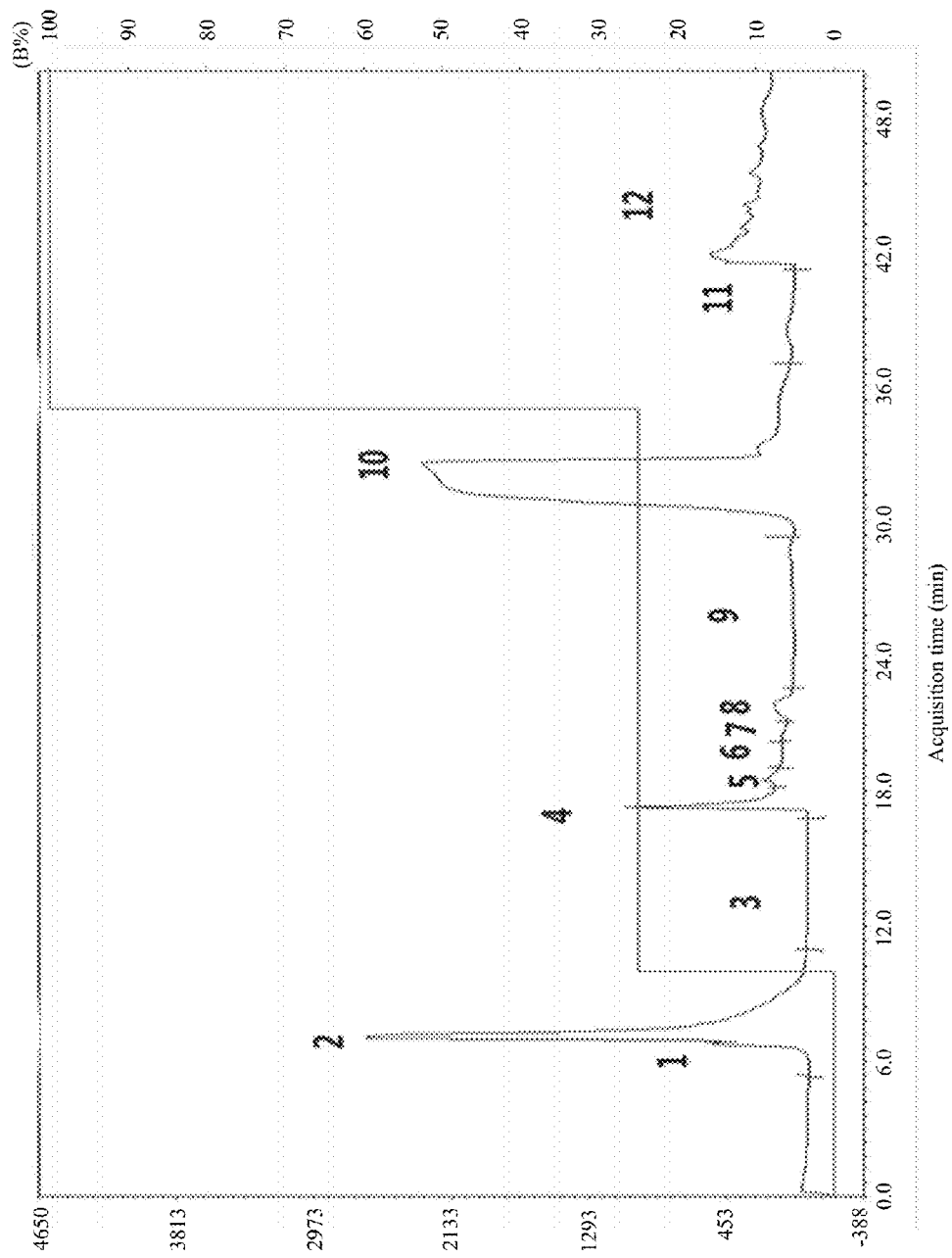
FIG. 19 is a DAC 150 normal-phase chromatography in accordance with one embodiment of the invention, in which, an abscissa represents an acquisition time (min), an ordinate represents a signal intensity (MV), a curve represents a chromatography curve, and a straight broken line represents a mixing concentration of a mobile phase.

The crude extract of C310-6 was completely dissolved in a mobile phase to prepare a solution having a concentration of 50 mg/mL. The solution was separated by a DAC 150 normal-phase preparative liquid chromatography column (250 mm×50 mm, 10 μm, 100 Å) with a detection wavelength of 260 nm, and then conducted with the elution separation using an A-B binary mobile phase system. The mobile phase A and the mobile phase B were n-hexane and ethyl acetate respectively. The gradient elution was employed for 60 min using 100% n-hexane and 100% ethyl acetate, and a flow rate was controlled at 700 mL/min, and an injection volume was 180 mL. The chromatogram was illustrated in FIG. 19. A tenth peak in FIG. 19 was collected, and was dried to acquire the intermediate component of C310-6.

Preparation of C310-6

Figure 20:
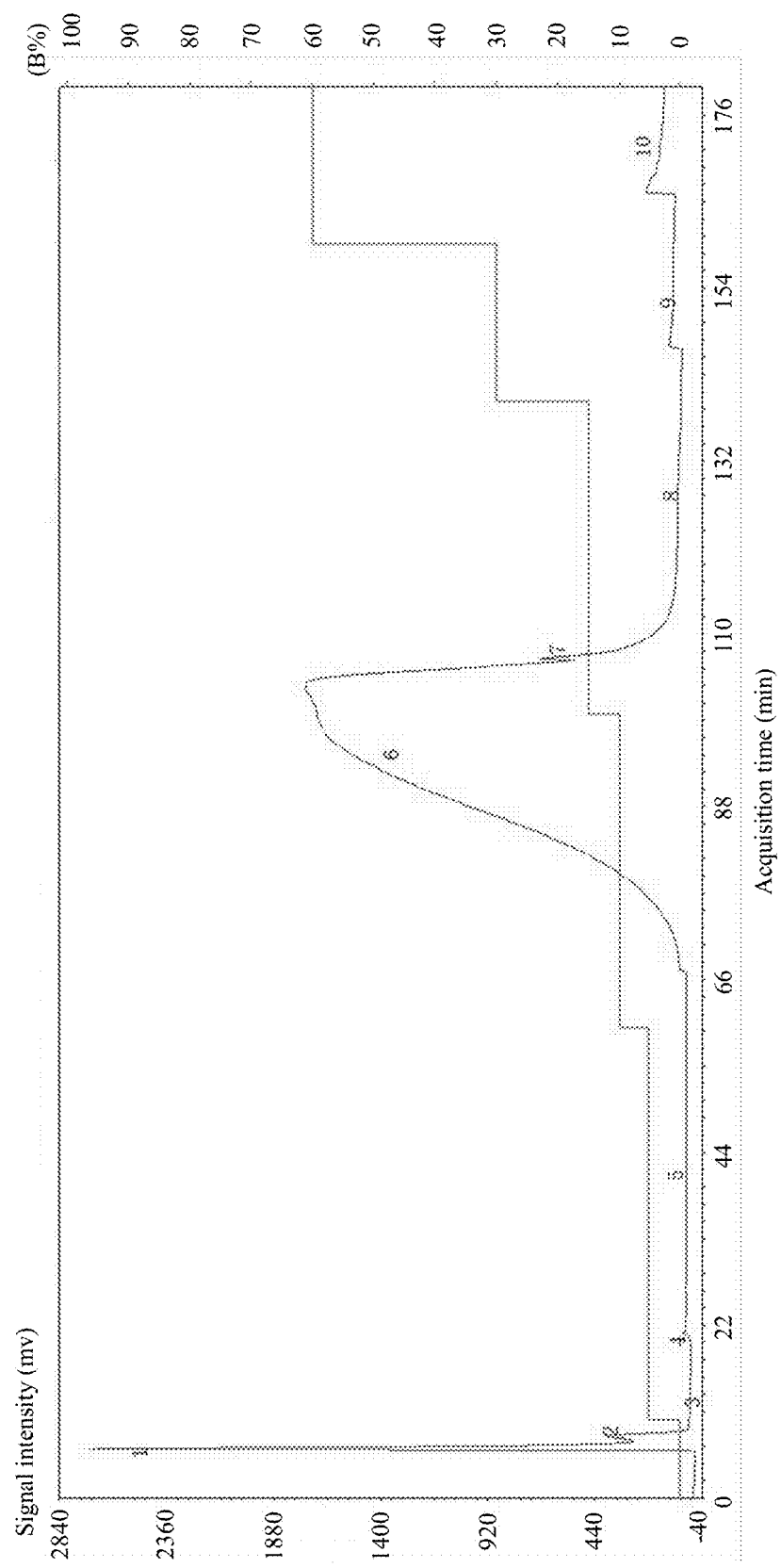
FIG. 20 is a DAC 50 normal-phase chromatography in accordance with one embodiment of the invention, in which, an abscissa represents an acquisition time (min), an ordinate represents a signal intensity (MV), a curve represents a chromatography curve, and a straight broken line represents a mixing concentration of a mobile phase.

The intermediate component of C310-6 was completely dissolved in a mobile phase to prepare a solution having a concentration of 33 mg/mL. The solution was separated by the DAC 150 normal-phase preparative liquid chromatography column (250 mm×50 mm, 10 μm, 100 Å) with a detection wavelength of 260 nm, and then conducted with the elution separation using an A-B binary mobile phase system. The mobile phase A and the mobile phase B were combinations of n-hexane and ethyl acetate. The gradient elution was employed for 180 min using 100% n-hexane and 100% ethyl acetate, and a flow rate was controlled at 700 mL/min, and an injection volume was 300 mL. The chromatogram was illustrated in FIG. 20. A sixth peak in FIG. 20 was collected, and was dried to acquire the compound C310-6, which was measured to be 7.2 g.

Example 2

Preparation of Crystals of C310-6

150 mg of (3α,9β,10α,13α,14β,17α,20S,22E)-ergosta-5,7,22-trien-3-ol obtained from Example 1 was added to 3 mL of a solvent. The solvent was 50% n-hexane-tetrahydrofuran solution. A resulting solution was allowed to stand at a temperature of 16° C. for natural evaporation and crystallization. When the solution was evaporated to ⅓ volume of an original volume, and crystals was collected from a bottom of a container, so that monoclinic crystals were obtained. The monoclinic crystals were leached and then washed by n-hexane at a temperature of −20° C. The monoclinic crystals of (3α,9β,10α,13α,14β,17α,20S,22E)-ergosta-5,7,22-trien-3-ol were directly analyzed by X-ray crystallography after the washing.

Example 3

Structure Identification of C310-6

1. Purity Analysis by High-Performance Liquid Chromatography (HPLC)

The component C310-6 was completely dissolved by 50% n-hexane-ethanol solution to prepare a solution having a concentration of 5 mg/mL, and the solution was thereafter performed with purity analysis by HPLC. The Kromasil normal-phase chromatography column (250 mm×4.6 mm, 5 μm, 100 Å) was employed, a detection wavelength was regulated to be 260 nm, and detection conditions were as follows: mobile phases were n-hexane and ethanol, the elution mode was gradient elution with 100% n-hexane-100% ethanol for 30 min, the flow rate was controlled at 1 mL/min, the injection volume was 20 μL, the temperature was 30° C., and a purity detected by the HPLC reached 99%, and HPLC chromatogram was shown in FIG. 1.

2. Mass Spectrometry

Figure 2:
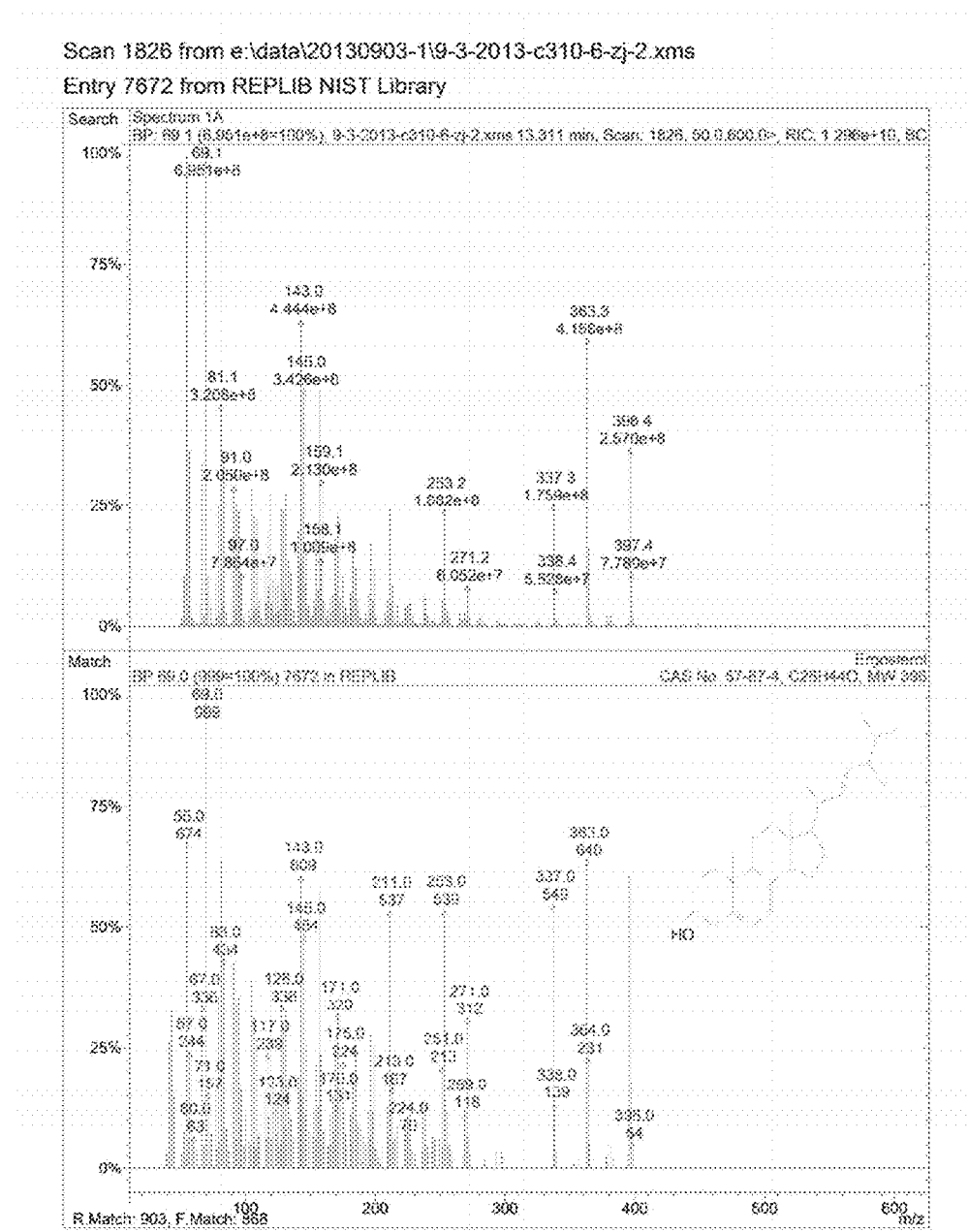
FIG. 2 is an electron impact mass spectra (EI-MS) analysis chart of compound C310-6 in accordance with one embodiment of the invention.

The compound C310-6 was performed with electron impact mass spectra (EI-MS) analysis using a gas chromatography Varian 450-GC provided by Hanmeng biotechnology (Tianjin) Co., Ltd., m/z 396.4 (M+H)$^+$, an implied molecular formula was $C_{28}H_{44}O$, and a mass spectrogram was shown in FIG. 2.

3. Infrared Spectrum Analysis

Figure 3:
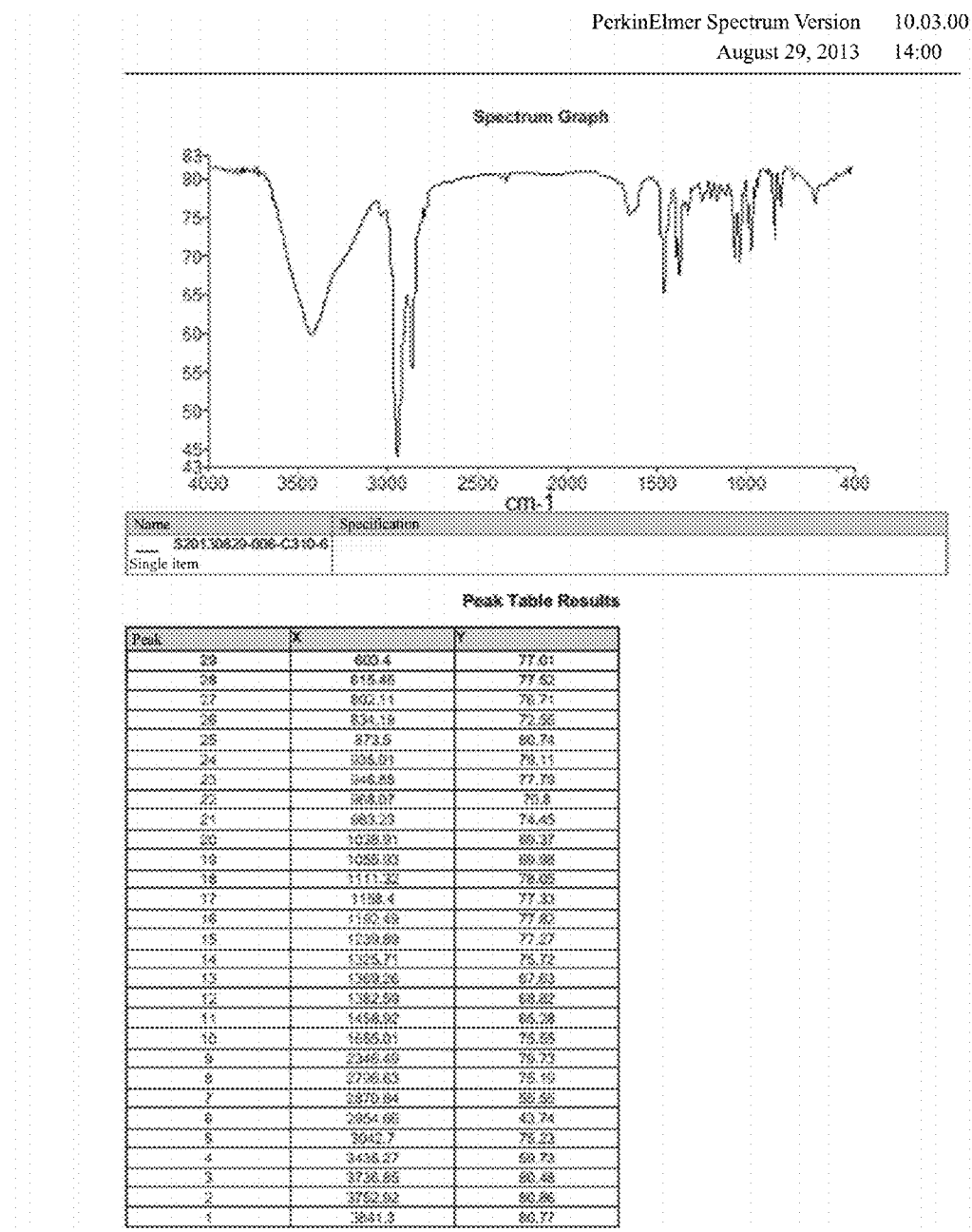
FIG. 3 is an infrared spectrum chart of compound C310-6 in accordance with one embodiment of the invention.
Figure 4A:
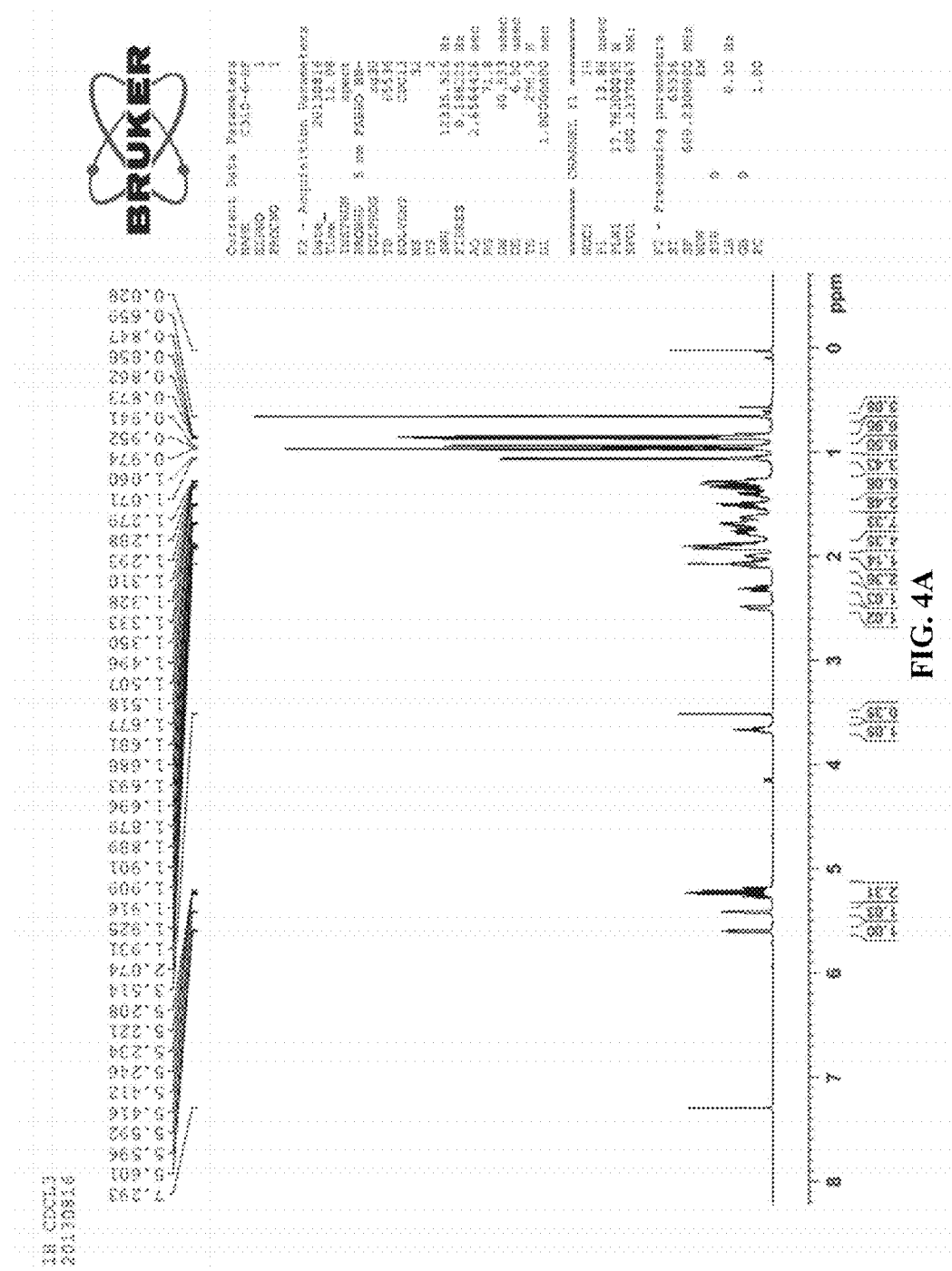
Figure 4B:
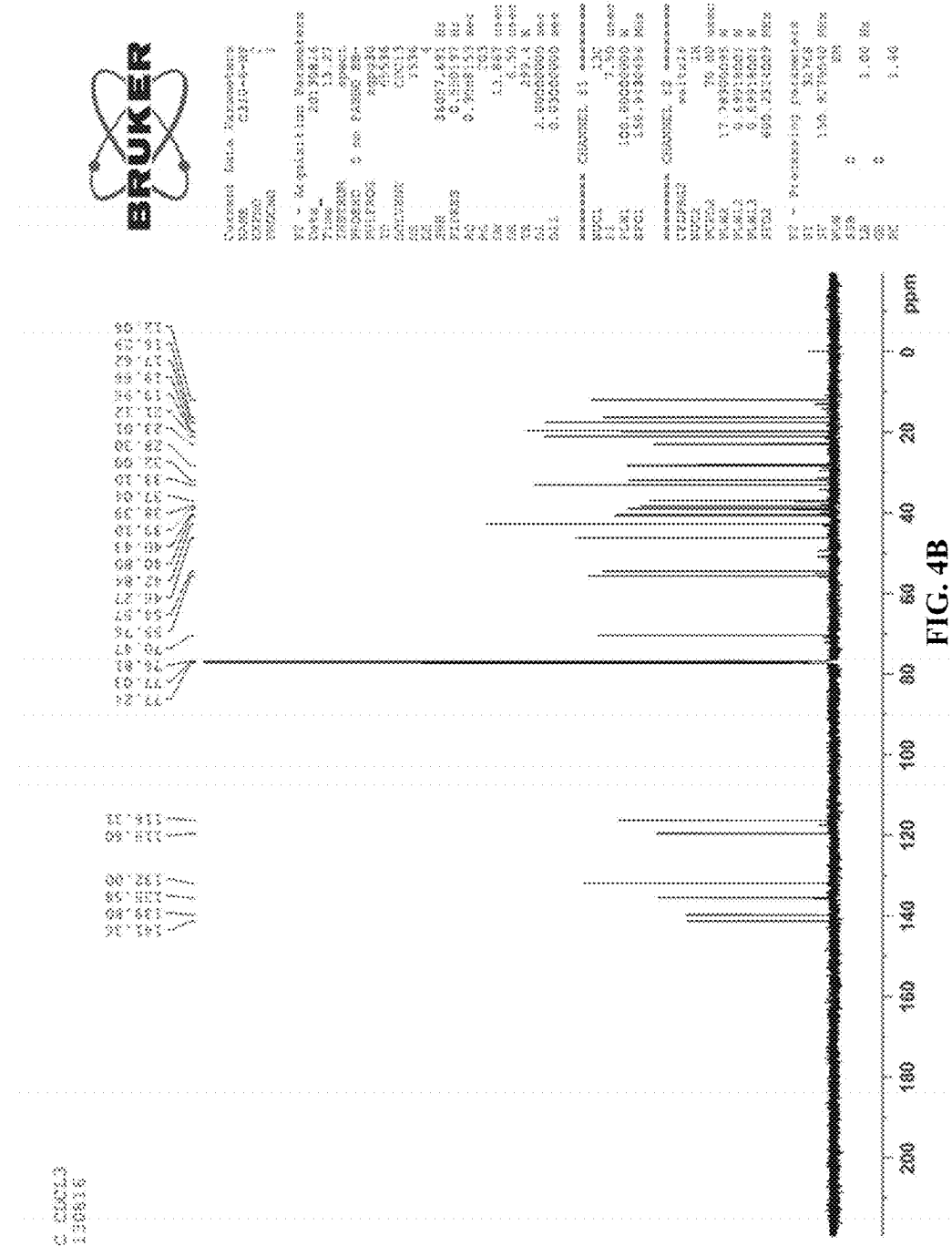
Figure 4C:
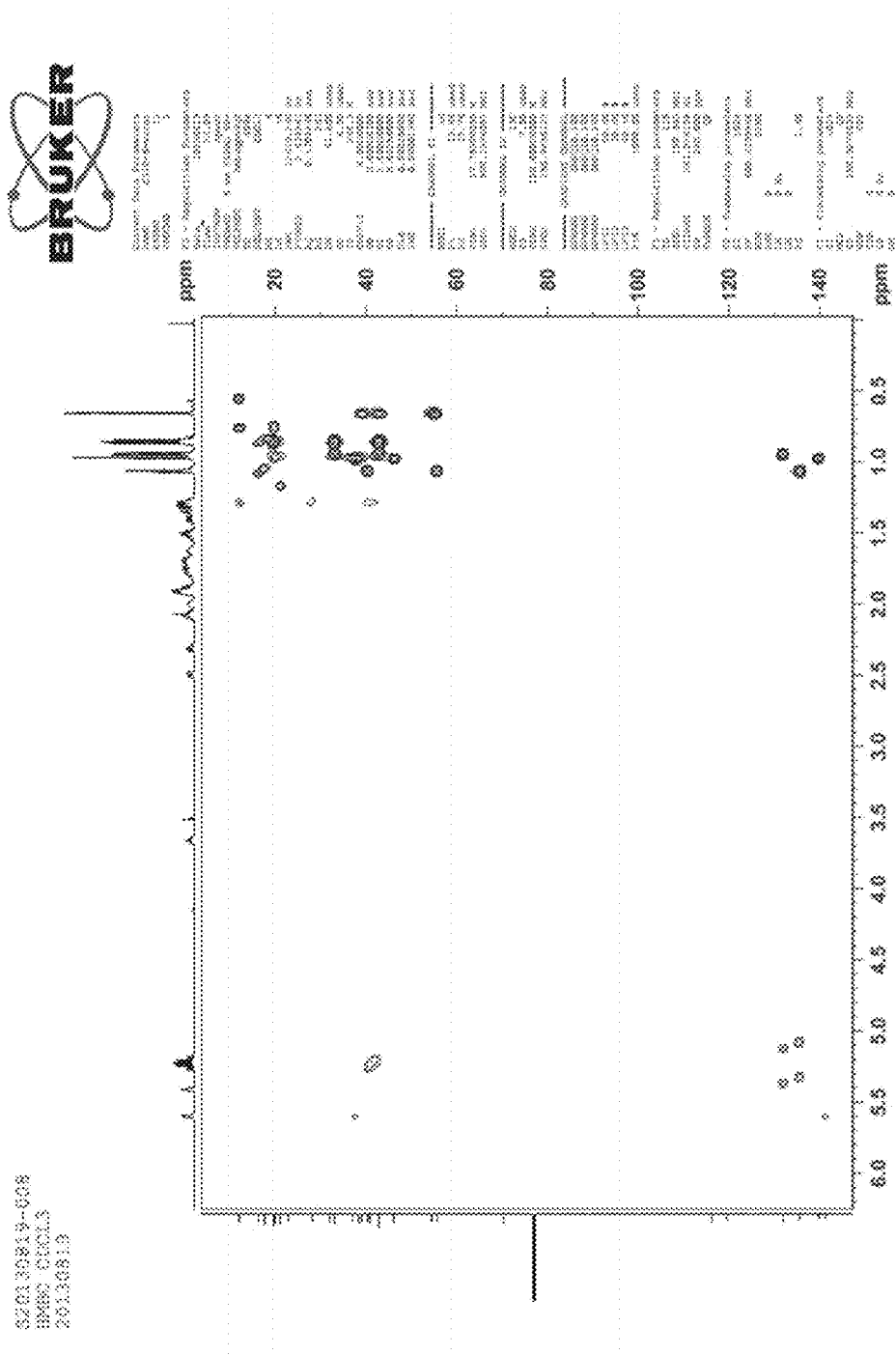
Figure 4D:
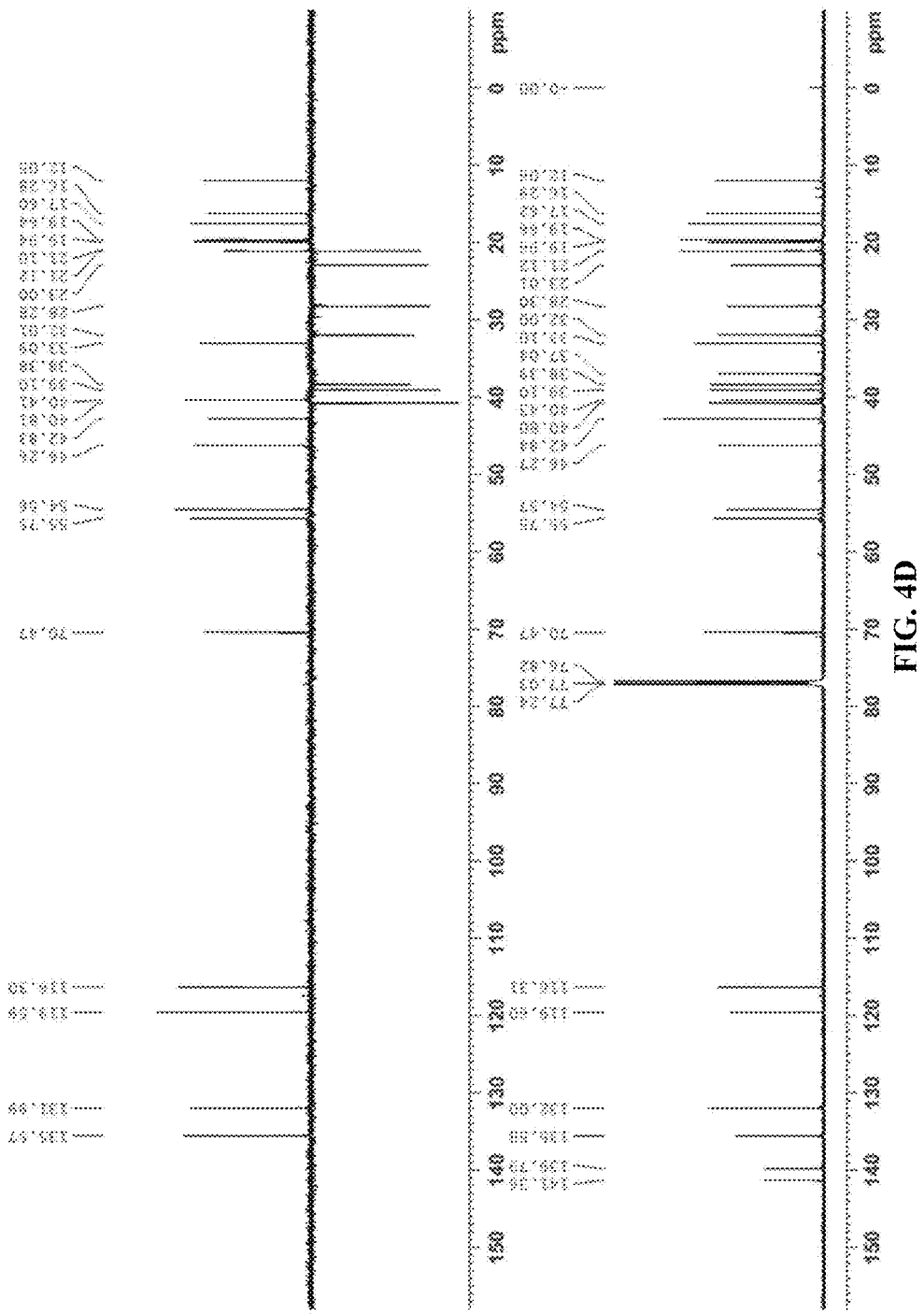

The compound C310-6 was performed with infrared spectrum analysis using a Fourier transform infrared spectrometer provided by Hanmeng biotechnology (Tianjin) Co., Ltd., cm$^{-1}$: 3841.3, 3752.92, 3736.85, 3435.27, 3042.7, 2954.66, 2870.84, 2796.63, 2346.49, 1655.01, 1458.92, 1382.59, 1369.26, 1325.71, 1239.89, 1192.49, 1158.4, 1111.32, 1055.93, 1038.91, 983.23, 968.07, 946.85, 935.01, 873.5, 834.19, 802.11, 615.46, 603.4, and the infrared spectrum was shown in FIG. 3.

4. NMR Analysis

The NMR analysis of C310-6 was performed with an NMR spectrometer Bruker A.G AVIII 600PLUS provided by Hanmeng biotechnology (Tianjin) Co., Ltd. The NMR spectrum was shown in FIGS. 4A, 4B, 4C, and 4D, and NMR data of the compound C310-6 acquired from the spectrums $^1$H NMR, $^{13}$C NMR, and HMBC were listed in Table 1.

TABLE 1

$^1$H NMR (600 MHz, J in Hz) and
$^{13}$C NMR (150 MHz) (CDCl3, TMS, ppm)

| Position | H | C |
|---|---|---|
| CH2(1) | 1.345, 1.933 | 38.39 |
| CH2(2) | 1.895, 1.994 | 32.00 |
| H—C(3) | 3.663 | 70.48 |
| CH2(4) | 2.488 | 40.81 |

TABLE 1-continued $^1$H NMR (600 MHz, J in Hz) and
$^{13}$C NMR (150 MHz) (CDCl3, TMS, ppm)

| Position | H | C |
|---|---|---|
| C(5) | | 139.80 |
| H—C(6) | 5.599(dd, J = 5.6, 2.4) | 119.61 |
| H—C(7) | 5.409(dt, J = 5.5, 2.7) | 116.31 |
| C(8) | | 141.37 |
| H—C(9) | 1.994 | 46.27 |
| C(10) | | 37.05 |
| CH2(11) | 1.56, 1.70 | 21.13 |
| CH2(12) | 2.062, 1.269 | 39.11 |
| C(13) | | 42.85 |
| H—C(14) | 1.919 | 54.58 |
| CH2(15) | 1.633, 1.351 | 23.01 |
| CH2(16) | 1.790, 1.339 | 28.30 |
| H—C(17) | 1.320 | 55.76 |
| CH3(18) | 0.62 | 12.06 |
| CH3(19) | 0.98 | 16.30 |
| H—C(20) | 2.49(m, 14.4, 4.6) | 40.43 |
| CH3(21) | 0.99, 1.15, 1.70 | 21.12 |
| H—C(22) | 5.22 (qd, J = 5.23) | 135.58 |
| H—C(23) | 5.22 (qd, J = 5.23) | 132.00 |
| H—C(24) | 1.86 | 42.84 |
| H—C(25) | 1.54, 1.46 | 33.11 |
| CH3(26) | 0.78 | 19.97 |
| CH3(27) | 0.94 | 19.66 |
| CH3(28) | 0.88 | 17.62 |

5. Identification of Crystal Structure

Figure 5:
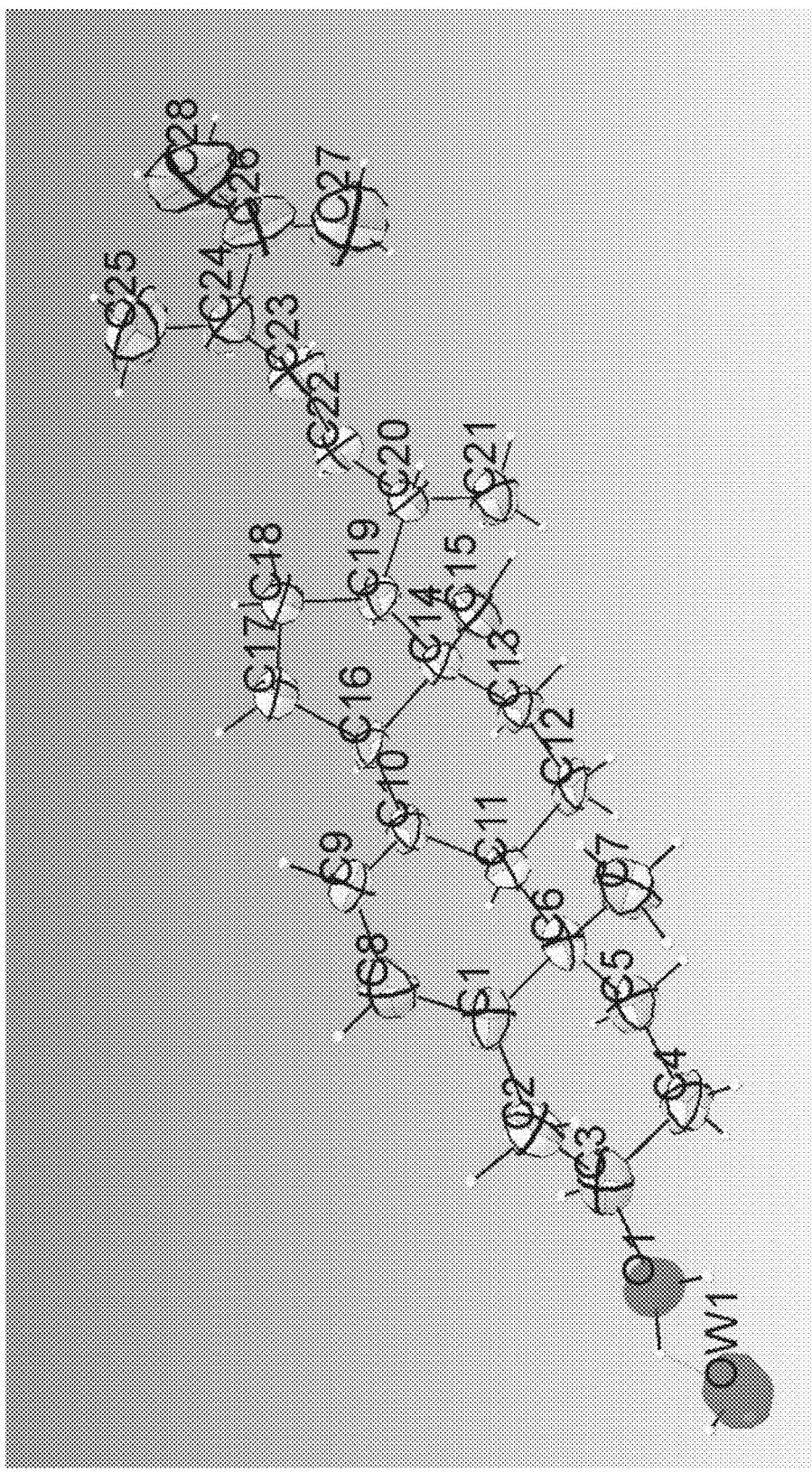
FIG. 5 is a molecular structure of a single crystal type of C310-6 in accordance with one embodiment of the invention.

The compound C310-6 after being washed was then dried and directly analyzed using an X-ray diffractometer provided by Tianjin University—State engineering technology research center of industrialization of crystallization technology. The monoclinic crystal of (3α,9β,10α,13α,14β,17α,20S,22E)-ergosta-5,7,22-trien-3-ol having a dimension of 0.25×0.20×0.15 mm was placed on the X-ray diffractometer. A graphite monochromatic Mo-Kα ray (λ=0.71073 A) was applied in a ω-θ scan mode within a range of 3.22°≤2θ≤25.50° to collect 21387 diffraction data and 9082 independent diffraction spots (R(int)=0.1150). The collected data were corrected by Lp factor and empirical absorption correction. The direct method and several rounds of difference Fourier synthesis were applied to find all the hydrogen atoms. The coordinates of the hydrogen atoms were obtained by geometric hydrogenation. The coordinates of all the hydrogen atoms and the anisotropic temperature factors thereof were all modified by the full-matrix least-square method. All the structure calculations were executed by the program SHELX-97, and the result shown that the molecular formula of the C310-6 was $C_{28}H_{44}O$. Specific data were listed in Tables 2-4, and the structural formula was shown in FIG. 5.

TABLE 2

Crystal data and structural parameters of monocrystal

| Object | Crystal data and structural parameters | Object | Crystal data and structural parameters |
|---|---|---|---|
| Empirical form μLa | C28H44O•H2O | Limiting indices | −11 <= h <= 11, −8 <= k <= 9, −42 <= l <= 42 |
| Form μLa weight | 414.65 | Reflections collected/unique | 21387/9082 (R(int) = 0.1150) |
| Temperature | 293(2) K | Completeness to theta = 25.50 | 99.7% |
| Wavelength | 0.71073 Å | Absorption correction | None |
| Crystal system, space group | Monoclinic, P2(1) | Max. and min. transmission | Max. and min. transmission |
| Unit cell dimensions | a = 9.848(2) Å alpha = 90 deg. b = 7.5529(15) Å beta = 95.62(3) deg. c = 35.074(7) Å gamma = 90 deg. | Refinement method | F μL1-matrix least-squares on F2 |
| Volume | 2596.2(9) A3 | Data/restraints/parameters | 9082/2/557 |
| Z, Calc μLated density | 4, 1.061 Mg/m3 | Goodness-of-fit on F2 | 0.962 |
| Absorption coefficient | 0.064 mm−1 | Final R indices (I > 2sigma(I)) | R1 = 0.0959, wR2 = 0.1863 |
| F(000) | 920 | R indices (all data) | R1 = 0.2094, wR2 = 0.2307 |
| Crystal size | 0.25 × 0.20 × 0.15 mm | Absolute structure parameter | 6(3) |
| Theta range for data collection | 3.22 to 25.50 deg. | Largest diff. peak and hole | 0.188 and −0.225 e. Å −3 |

TABLE 3

| Bond lengths of monocrystal | | | | | | |
|---|---|---|---|---|---|---|
| O(1)—C(3) | 1.428(6) | C(13)—H(13A) | 0.9700 | C(5)—H(5B) | 0.9700 | C(21)—H(21A) | 0.9600 |
| O(1)—H(1A) | 0.8200 | C(13)—H(13B) | 0.9700 | C(6)—C(7) | 1.528(7) | C(21)—H(21B) | 0.9600 |
| O(1)—HW1A | 1.29(8) | C(14)—C(15) | 1.512(6) | C(6)—C(11) | 1.553(6) | C(21)—H(21C) | 0.9600 |
| OW1—HW1B | 0.86(8) | C(14)—C(16) | 1.523(7) | C(7)—H(7A) | 0.9600 | C(22)—C(23) | 1.314(7) |
| O(2)—C(31) | 1.433(6) | C(14)—C(19) | 1.548(6) | C(7)—H(7B) | 0.9600 | C(22)—H(22A) | 0.9300 |
| O(2)—H(2A) | 0.8200 | C(15)—H(15A) | 0.9600 | C(7)—H(7C) | 0.9600 | C(23)—C(24) | 1.494(8) |
| OW2—HW2A | 1.26(16) | C(15)—H(15B) | 0.9600 | C(8)—C(9) | 1.447(7) | C(23)—H(23A) | 0.9300 |
| OW2—HW2B | 1.18(18) | C(15)—H(15C) | 0.9600 | C(8)—H(8A) | 0.9300 | C(24)—C(25) | 1.514(11) |
| C(1)—C(8) | 1.340(7) | C(16)—C(17) | 1.523(6) | C(9)—C(10) | 1.325(7) | C(24)—C(26) | 1.537(11) |
| C(1)—C(6) | 1.503(7) | C(16)—H(16A) | 0.9800 | C(9)—H(9A) | 0.9300 | C(24)—H(24A) | 0.9800 |
| C(1)—C(2) | 1.515(7) | C(17)—C(18) | 1.546(7) | C(10)—C(16) | 1.486(7) | C(25)—H(25A) | 0.9600 |
| C(2)—C(3) | 1.487(7) | C(17)—H(17A) | 0.9700 | C(10)—C(11) | 1.521(6) | C(25)—H(25B) | 0.9600 |
| C(2)—H(2B) | 0.9700 | C(17)—H(17B) | 0.9700 | C(11)—C(12) | 1.539(7) | C(25)—H(25C) | 0.9600 |
| C(2)—H(2C) | 0.9700 | C(18)—C(19) | 1.530(7) | C(11)—H(11A) | 0.9800 | C(26)—C(28) | 1.478(10) |
| C(3)—C(4) | 1.503(8) | C(18)—H(18A) | 0.9700 | C(12)—C(13) | 1.534(6) | C(26)—C(27) | 1.503(14) |
| C(3)—H(3A) | 0.9800 | C(18)—H(18B) | 0.9700 | C(12)—H(12A) | 0.9700 | C(26)—H(26A) | 0.9800 |
| C(4)—C(5) | 1.524(6) | C(19)—C(20) | 1.544(7) | C(12)—H(12B) | 0.9700 | C(27)—H(27A) | 0.9600 |
| C(4)—H(4A) | 0.9700 | C(19)—H(19A) | 0.9800 | C(13)—C(14) | 1.520(7) | C(27)—H(27B) | 0.9600 |
| C(4)—H(4B) | 0.9700 | C(20)—C(22) | 1.485(7) | C(27)—H(27C) | 0.9600 | C(28)—H(28B) | 0.9600 |
| C(5)—C(6) | 1.534(7) | C(20)—C(21) | 1.536(8) | C(28)—H(28A) | 0.9600 | C(28)—H(28C) | 0.9600 |
| C(5)—H(5A) | 0.9700 | C(20)—H(20A) | 0.9800 | | | | |

TABLE 4

| Bond angles of monocrystals | | | | | | |
|---|---|---|---|---|---|---|
| C(3)—O(1)—H(1A) | 109.5 | C(6)—C(7)—H(7B) | 109.5 | H(15A)—C(15)—H(15C) | 109.5 |
| C(3)—O(1)—HW1A | 115(3) | H(7A)—C(7)—H(7B) | 109.5 | H(15B)—C(15)—H(15C) | 109.5 |
| H(1A)—O(1)—HW1A | 109.1 | C(6)—C(7)—H(7C) | 109.5 | C(10)—C(16)—C(14) | 115.1(4) |
| C(31)—O(2)—H(2A) | 109.5 | H(7A)—C(7)—H(7C) | 109.5 | C(10)—C(16)—C(17) | 118.6(4) |
| HW2A—OW2—HW2B | 56(8) | H(7B)—C(7)—H(7C) | 109.5 | C(14)—C(16)—C(17) | 104.5(4) |
| C(8)—C(1)—C(6) | 120.7(5) | C(1)—C(8)—C(9) | 122.1(5) | C(10)—C(16)—H(16A) | 105.9 |
| C(8)—C(1)—C(2) | 121.1(5) | C(1)—C(8)—H(8A) | 119.0 | C(14)—C(16)—H(16A) | 105.9 |
| C(6)—C(1)—C(2) | 117.8(5) | C(9)—C(8)—H(8A) | 119.0 | C(17)—C(16)—H(16A) | 105.9 |
| C(3)—C(2)—C(1) | 113.9(5) | C(10)—C(9)—C(8) | 121.7(5) | C(16)—C(17)—C(18) | 103.2(4) |
| C(3)—C(2)—H(2B) | 108.8 | C(10)—C(9)—H(9A) | 119.1 | C(16)—C(17)—H(17A) | 111.1 |
| C(1)—C(2)—H(2B) | 108.8 | C(8)—C(9)—H(9A) | 119.1 | C(18)—C(17)—H(17A) | 111.1 |
| C(3)—C(2)—H(2C) | 108.8 | C(9)—C(10)—C(16) | 123.5(4) | C(16)—C(17)—H(17B) | 111.1 |
| C(1)—C(2)—H(2C) | 108.8 | C(9)—C(10)—C(11) | 119.6(4) | C(18)—C(17)—H(17B) | 111.1 |
| H(2B)—C(2)—H(2C) | 107.7 | C(16)—C(10)—C(11) | 115.7(4) | H(17A)—C(17)—H(17B) | 109.1 |
| O(1)—C(3)—C(2) | 108.1(4) | C(10)—C(11)—C(12) | 113.0(4) | C(19)—C(18)—C(17) | 107.5(4) |
| O(1)—C(3)—C(4) | 112.0(4) | C(10)—C(11)—C(6) | 113.7(4) | C(19)—C(18)—H(18A) | 110.2 |
| C(2)—C(3)—C(4) | 110.9(5) | C(12)—C(11)—C(6) | 112.4(4) | C(17)—C(18)—H(18A) | 110.2 |
| O(1)—C(3)—H(3A) | 108.6 | C(10)—C(11)—H(11A) | 105.6 | C(19)—C(18)—H(18B) | 110.2 |
| C(2)—C(3)—H(3A) | 108.6 | C(12)—C(11)—H(11A) | 105.6 | C(17)—C(18)—H(18B) | 110.2 |
| C(4)—C(3)—H(3A) | 108.6 | C(6)—C(11)—H(11A) | 105.6 | H(18A)—C(18)—H(18B) | 108.5 |
| C(3)—C(4)—C(5) | 110.0(4) | C(13)—C(12)—C(11) | 115.1(4) | C(18)—C(19)—C(20) | 111.4(4) |
| C(3)—C(4)—H(4A) | 109.7 | C(13)—C(12)—H(12A) | 108.5 | C(18)—C(19)—C(14) | 103.4(4) |
| C(5)—C(4)—H(4A) | 109.7 | C(11)—C(12)—H(12A) | 108.5 | C(20)—C(19)—C(14) | 119.0(4) |
| C(3)—C(4)—H(4B) | 109.7 | C(13)—C(12)—H(12B) | 108.5 | C(18)—C(19)—H(19A) | 107.5 |
| C(5)—C(4)—H(4B) | 109.7 | C(11)—C(12)—H(12B) | 108.5 | C(20)—C(19)—H(19A) | 107.5 |
| H(4A)—C(4)—H(4B) | 108.2 | H(12A)—C(12)—H(12B) | 107.5 | C(14)—C(19)—H(19A) | 107.5 |
| C(4)—C(5)—C(6) | 114.7(5) | C(14)—C(13)—C(12) | 111.9(4) | C(22)—C(20)—C(21) | 109.5(5) |
| C(4)—C(5)—H(5A) | 108.6 | C(14)—C(13)—H(13A) | 109.2 | C(22)—C(20)—C(19) | 110.9(4) |
| C(6)—C(5)—H(5A) | 108.6 | C(12)—C(13)—H(13A) | 109.2 | C(21)—C(20)—C(19) | 112.4(5) |
| C(4)—C(5)—H(5B) | 108.6 | C(14)—C(13)—H(13B) | 109.2 | C(22)—C(20)—H(20A) | 108.0 |
| C(6)—C(5)—H(5B) | 108.6 | C(12)—C(13)—H(13B) | 109.2 | C(21)—C(20)—H(20A) | 108.0 |
| H(5A)—C(5)—H(5B) | 107.6 | H(13A)—C(13)—H(13B) | 107.9 | C(19)—C(20)—H(20A) | 108.0 |
| C(1)—C(6)—C(7) | 105.6(4) | C(15)—C(14)—C(13) | 111.1(4) | C(20)—C(21)—H(21A) | 109.5 |
| C(1)—C(6)—C(5) | 109.4(4) | C(15)—C(14)—C(16) | 111.8(4) | C(20)—C(21)—H(21B) | 109.5 |
| C(7)—C(6)—C(5) | 110.5(5) | C(13)—C(14)—C(16) | 105.3(4) | H(21A)—C(21)—H(21B) | 109.5 |
| C(1)—C(6)—C(11) | 111.7(4) | C(15)—C(14)—C(19) | 110.7(4) | C(14)—C(15)—H(15B) | 109.5 |
| C(7)—C(6)—C(11) | 111.8(4) | C(13)—C(14)—C(19) | 116.8(4) | C(24)—C(23)—H(23A) | 116.5 |
| C(5)—C(6)—C(11) | 107.8(4) | C(16)—C(14)—C(19) | 100.6(4) | C(23)—C(24)—C(25) | 109.4(7) |
| C(6)—C(7)—H(7A) | 109.5 | C(14)—C(15)—H(15A) | 109.5 | C(23)—C(24)—C(26) | 110.0(6) |
| C(20)—C(21)—H(21C) | 109.5 | H(28A)—C(28)—H(28C) | 109.5 | C(25)—C(24)—C(26) | 112.7(8) |
| H(21A)—C(21)—H(21C) | 109.5 | H(28B)—C(28)—H(28C) | 109.5 | C(23)—C(24)—H(24A) | 108.2 |
| H(21B)—C(21)—H(21C) | 109.5 | C(22)—C(23)—C(24) | 127.0(6) | C(25)—C(24)—H(24A) | 108.2 |
| C(23)—C(22)—C(20) | 125.3(6) | C(14)—C(15)—H(15B) | 109.5 | C(26)—C(24)—H(24A) | 108.2 |
| C(23)—C(22)—H(22A) | 117.4 | H(15A)—C(15)—H(15B) | 109.5 | C(24)—C(25)—H(25A) | 109.5 |
| C(20)—C(22)—H(22A) | 117.4 | C(14)—C(15)—H(15C) | 109.5 | C(24)—C(25)—H(25B) | 109.5 |
| H(25A)—C(25)—H(25B) | 109.5 | | | | |
| C(24)—C(25)—H(25C) | 109.5 | | | | |
| H(25A)—C(25)—H(25C) | 109.5 | | | | |
| H(25B)—C(25)—H(25C) | 109.5 | | | | |
| C(28)—C(26)—C(27) | 109.7(10) | | | | |

TABLE 4-continued

Bond angles of monocrystals

| | |
|---|---|
| C(28)—C(26)—C(24) | 112.4(9) |
| C(27)—C(26)—C(24) | 112.4(9) |
| C(28)—C(26)—H(26A) | 107.3 |
| C(27)—C(26)—H(26A) | 107.3 |
| C(24)—C(26)—H(26A) | 107.3 |
| C(26)—C(27)—H(27A) | 109.5 |
| C(26)—C(27)—H(27B) | 109.5 |
| H(27A)—C(27)—H(27B) | 109.5 |
| C(26)—C(27)—H(27C) | 109.5 |
| H(27A)—C(27)—H(27C) | 109.5 |
| H(27B)—C(27)—H(27C) | 109.5 |
| C(26)—C(28)—H(28A) | 109.5 |
| C(26)—C(28)—H(28B) | 109.5 |
| H(28A)—C(28)—H(28B) | 109.5 |
| C(26)—C(28)—H(28C) | 109.5 |
| C(20)—C(21)—H(21C) | 109.5 |
| H(21A)—C(21)—H(21C) | 109.5 |
| H(28A)—C(28)—H(28C) | 109.5 |
| H(28B)—C(28)—H(28C) | 109.5 |

Example 4

Cell Viability Tests of Single Crystal Compound C310-6

Experiment on Human Hepatoma Cells Hep-g2

1. Eight-well plate (E-Plate L8) supplied by ACEA Bio (Hangzhou) Co. Ltd. was combined with an iCELLigence real-time cell-analyzer (RTCA). 150 μL of a complete F-12K medium was added to each well and the eight-well plate was placed in an incubator at a temperature of 37° C. and an atmosphere of 5% $CO_2$, and the background data were regulated to 40-130. The compound C310-6 was fully dissolved by dimethyl sulfoxide to concentrations of 100 mg/mL, 50 mg/mL, 25 mg/mL, 12.5 mg/mL, 6.3 mg/mL, 3.1 mg/mL, and 1.6 mg/mL, and then diluted to by the complete F-12K medium obtain working solutions having concentrations of 10 mg/mL, 5 mg/mL, 2.5 mg/mL, 1.25 mg/mL, 0.63 mg/mL, 0.31 mg/mL, and 0.16 mg/mL. Well cultivated human hepatoma cells Hep-g2 were digested by trypsin and diluted into live cell suspensions with a concentration of $4 \times 10^4$/mL. Thereafter, 345 μL of the live cell suspension of C310-6 was inoculated to each well of an eight-well plate, and then 5 μL of the working solution was added to each well to enable final concentrations of the C310-6 compound to be 100 μg/mL, 50 μg/mL, 25 μg/mL, 12.5 μg/mL, 6.3 μg/mL, 3.1 μg/mL, and 1.6 μg/mL. An eighth hole was added with the complete F-12K medium containing 1 wt. % of dimethyl sulfoxide as a blank control group, and was displaced into the incubator at 37° C. and 5% $CO_2$ for 48 hrs.

Specific administration schemes were listed in Table 5.

TABLE 5

Experiment on human hepatoma cells Hep-g2

| | Hole Number | | | | | | | |
|---|---|---|---|---|---|---|---|---|
| | 1 | 2 | 3 | 4 | 5 | 6 | 7 | 8 |
| Sample | C310-6 | C310-6 | C310-6 | C310-6 | C310-6 | C310-6 | C310-6 | Complete F-12K medium of dimethyl sulfoxide |
| Sample concentration | 100 μg/mL | 50 μg/mL | 25 μg/mL | 12.5 μg/mL | 6.3 μg/mL | 3.1 μg/mL | 1.6 μg/mL | Complete F-12K medium containing 1 wt. ‰ of dimethyl sulfoxide |

Figure 6:
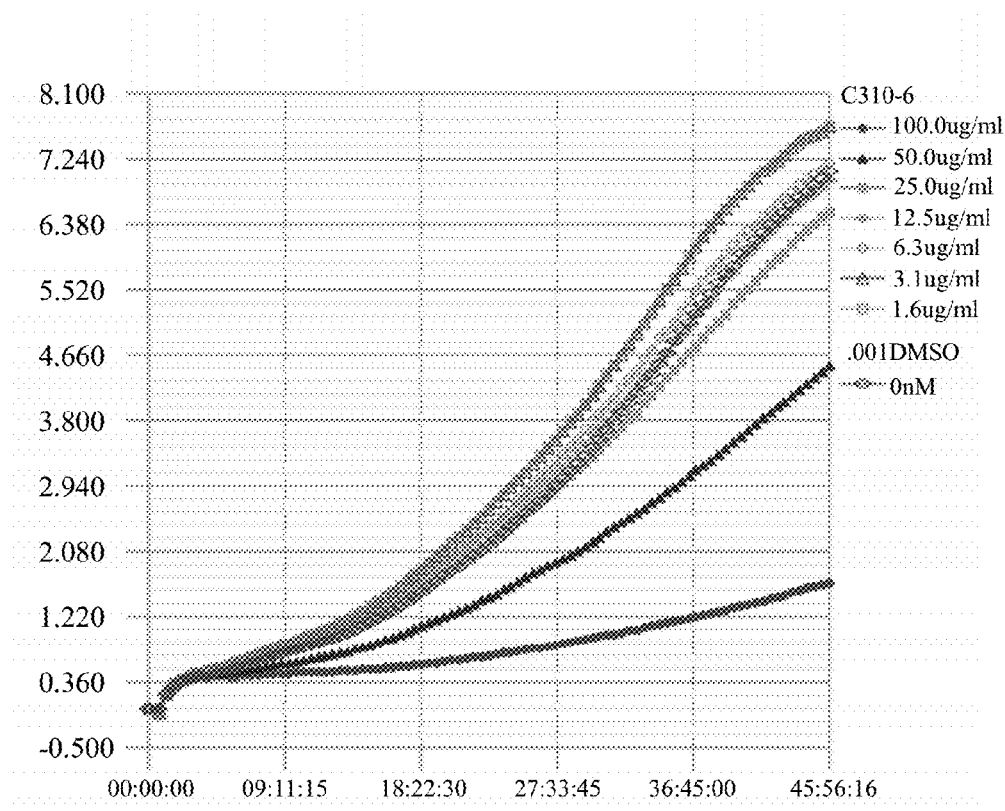
FIG. 6 is a real-time data monitoring chart showing growth of human liver cancer cells Hep-g2 inhibited by C310-6 of different concentrations.

Real-time data (48 hrs) were shown in FIG. 6 demonstrating growth of the human hepatoma cells Hep-g2 inhibited by C310-6 compound of different concentrations.

2. MTT Assay a. 250 mg of 3-(4,5-dimethylthiazol-2-yl)-2,5-diphenyltetrazolium bromide (MTT) was dissolved by 50 mL of phosphate buffered saline (PBS) having a concentration of 0.01 mol/L and PH=7.45 to yield a MTT solution having a final concentration of 5 mg/mL. The MTT solution was dispensed and protected against light at the temperature of −20° C. after filtration and sterilization.

b. A suspension of single cell line was prepared and inoculated into 96-well plate (cells were diluted to a concentration of $4 \times 10^4$/mL by the F-12K basic culture medium, 100 μL diluted cells were added to each well and cultivated at 37° C., 5% $CO_2$ for 20 hrs, each group was provided with 4 parallel samples).

c. The culture medium was removed; and new culture mediums were prepared according to serial concentration of the antitumor drug (C310-6), each well was added with 100 µL of the new culture medium and cells were cultivated for 48 hrs.

d. 20 µL of MTT solution having the concentration of 5 mg/mL was added to each well for incubating the cells for 4 hrs.

e. The culture medium in each hole was sucked out as completely as possible, 150 µL DMSO solution was added to each hole, and vibrated for 10 min to fully dissolve the crystals.

f. OD values were measured by a microplate reader, λ=490 nm g. A cell viability curve was charted, 1050 value was calculated to be 14.152 µg/mL, which means that the compound has excellent human hepatoma cells Hep-g2 activity resistance.

Experiment on Human Lung Cancer Cells A549

1. Eight-well plate (E-Plate L8) supplied by ACEA Bio (Hangzhou) Co. Ltd. was combined with an iCELLigence real-time cell-analyzer (RTCA). 150 µL of a complete MEM medium was added to each well and the eight-well plate was placed in an incubator at a temperature of 37° C. and an atmosphere of 5% $CO_2$, and the background data were regulated to 40-130. The compound C310-6 was fully dissolved by dimethyl sulfoxide to concentrations of 100 mg/mL, 50 mg/mL, 25 mg/mL, 12.5 mg/mL, 6.3 mg/mL, 3.1 mg/mL, and 1.6 mg/mL, and then diluted to by the complete MEM medium obtain working solutions having concentrations of 10 mg/mL, 5 mg/mL, 2.5 mg/mL, 1.25 mg/mL, 0.63 mg/mL, 0.31 mg/mL, and 0.16 mg/mL. Well cultivated human lung cancer cells Hep-g2 were digested by trypsin and diluted into live cell suspensions with a concentration of $4 \times 10^4$/mL. Thereafter, 345 µL of the live cell suspension of C310-6 was inoculated to each well of an eight-well plate, and then 5 µL of the working solution was added to each well to enable final concentrations of the C310-6 compound to be 100 µg/mL, 50 µg/mL, 25 µg/mL, 12.5 µg/mL, 6.3 µg/mL, 3.1 µg/mL, and 1.6 µg/mL. An eighth well was added with the complete MEM medium containing 1 wt. % of dimethyl sulfoxide as a blank control group, and was displaced into the incubator at 37° C. and 5% $CO_2$ for 48 hrs.

Specific administering schemes were listed in Table 6.

2. MTT Assay a. 250 mg of MTT was dissolved by 50 mL of PBS having a concentration of 0.01 mol/L and PH=7.45 to yield a MTT solution having a final concentration of 5 mg/mL. The MTT solution was dispensed and protected against light at the temperature of −20° C. after filtration and sterilization.

b. A suspension of single cell line was prepared and inoculated into 96-well plate (cells were diluted to a concentration of $3 \times 10^4$/mL by the MEM basic culture medium, 100 µL diluted cells were added to each well and cultivated at 37° C., 5% $CO_2$ for 20 hrs, each group was provided with 4 parallel samples).

c. The culture medium was removed; and new culture mediums were prepared according to serial concentration of the antitumor drug (C310-6), each well was added with 100 µL of the new culture medium and cells were cultivated for 48 hrs.

d. 20 µL of MTT solution having the concentration of 5 mg/mL was added to each well for incubating the cells for 4 hrs.

e. The culture medium in each hole was sucked out as completely as possible, 150 µL DMSO solution was added to each hole, and vibrated for 10 min to fully dissolve the crystals.

f. OD values were measured by a microplate reader, λ=490 nm g. A cell viability curve was charted, 1050 value was calculated to be 14.152 µg/mL, which means that the compound has excellent human hepatoma cells Hep-g2 activity resistance.

Example 5

Cell Viability Tests of Single Crystal of Compound C310-6

Antitumor Experiment of C310-6 Against $H_{22}$ Tumor Bearing Mice $H_{22}$ tumor bearing mice were adopted to observe the effect of the anti-liver cancer of five classes of mixtures.

Specific steps are as follows:

1. Construction of $H_{22}$ Tumor Bearing Mice $H_{22}$ tumor bearing mouse inoculated with the tumor for 8-13 days and in good condition was killed by dislocation. Body surface of the mouse was disinfected by alcohol. The tumors were separated from the mouse and placed in sterile petri dish containing normal saline in a sterile environment

TABLE 6

| Experiment on human lung cancer cells A549 | | | | | | | |
|---|---|---|---|---|---|---|---|
| Hole Number | | | | | | | |
| 1 | 2 | 3 | 4 | 5 | 6 | 7 | 8 |
| Sample | | | | | | | |
| C310-6 | C310-6 | C310-6 | C310-6 | C310-6 | C310-6 | C310-6 | Complete MEM medium of dimethyl sulfoxide |
| Sample concentration | | | | | | | |
| 100 µg/mL | 50 µg/mL | 25 µg/mL | 12.5 µg/mL | 6.3 µg/mL | 3.1 µg/mL | 1.6 µg/mL | Complete MEM medium containing 1 wt. ‰ of dimethyl sulfoxide |

Figure 7:
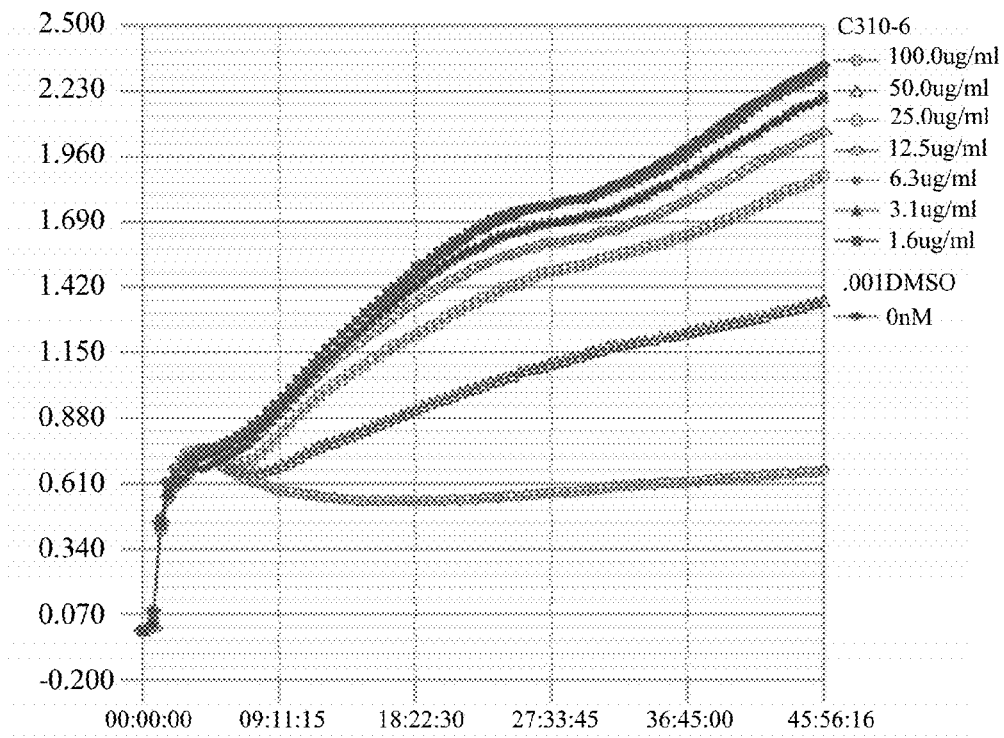
FIG. 7 is a real-time data monitoring chart showing growth of human lung cancer cells A549 inhibited by C310-6 of different concentrations.
Figure 8:
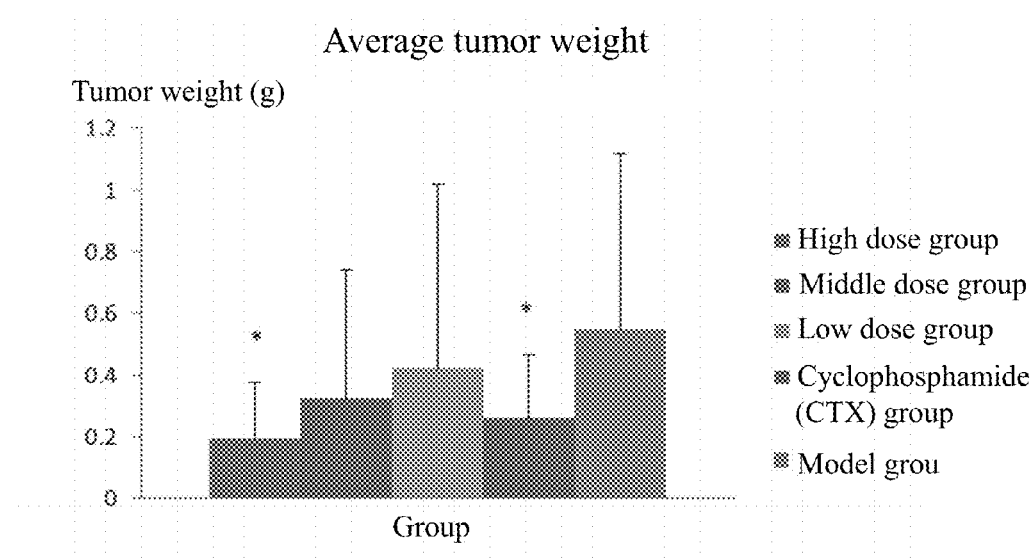
FIG. 8 is a chart showing an average tumor weight (g) of mice in antitumor experiment of C310-6 against $H_{22}$ tumor bearing mice, in which a high dose group, a middle dose group, a low dose group, a cyclophosphamide (CTX) group, and a model group are represented in sequence.
Figure 9:
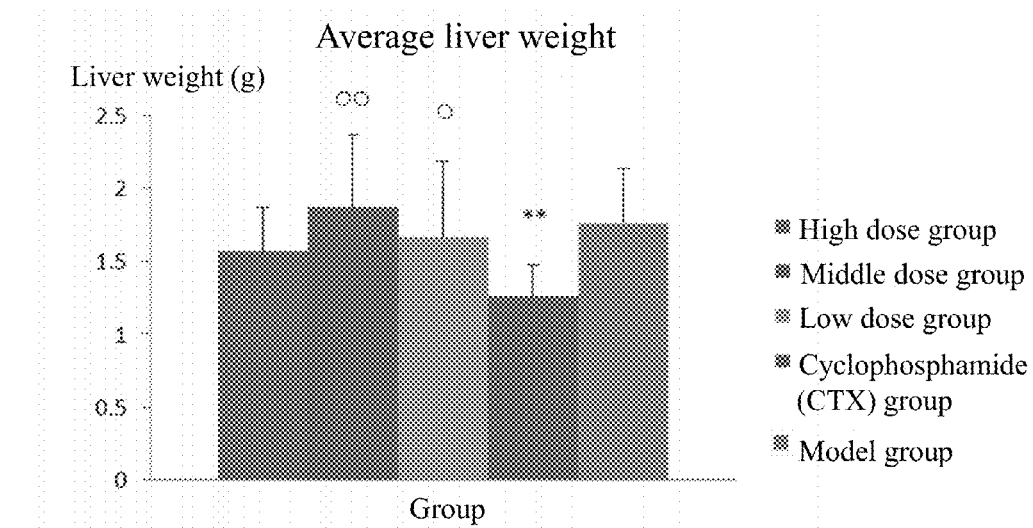
FIG. 9 is a chart showing an average liver weight (g) of mice in antitumor experiment of C310-6 against $H_{22}$ tumor bearing mice, in which a high dose group, a middle dose group, a low dose group, a CTX group, and a model group are represented in sequence.
Figure 10:
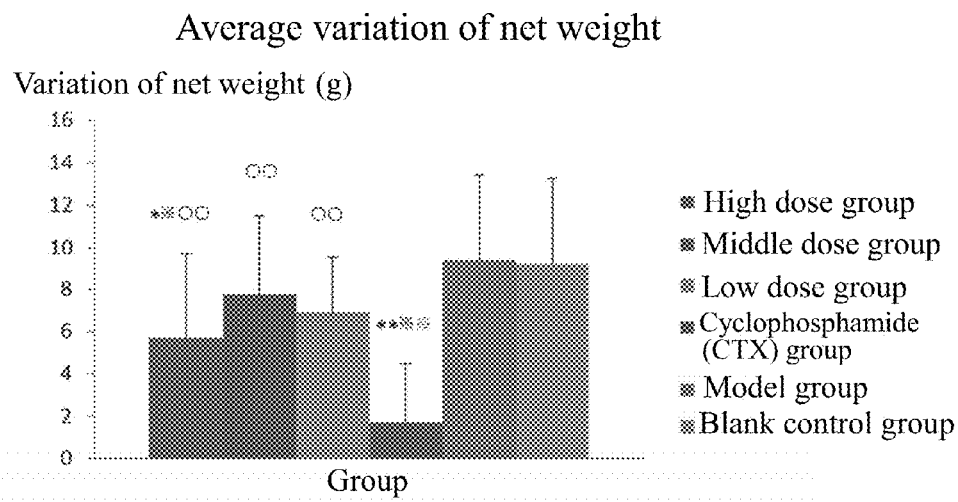
FIG. 10 is a chart showing an average variation of net weight (g) of mice in antitumor experiment of C310-6 against $H_{22}$ tumor bearing mice, in which a high dose group, a middle dose group, a low dose group, a CTX group, and a model group are represented in sequence.
Figure 11:
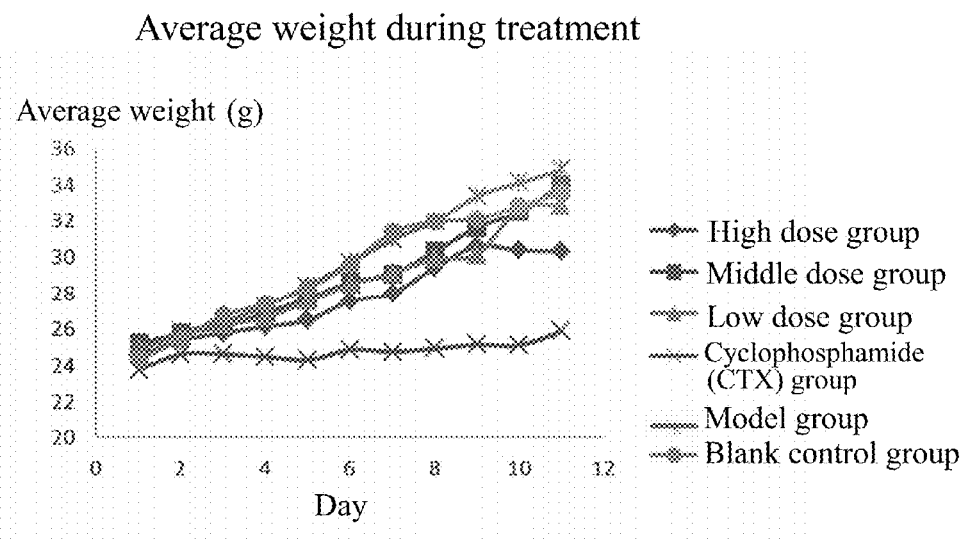
FIG. 11 shows an average weight variation of mice during treatment in antitumor experiment of C310-6 against $H_{22}$ tumor bearing mice.
Figure 12:
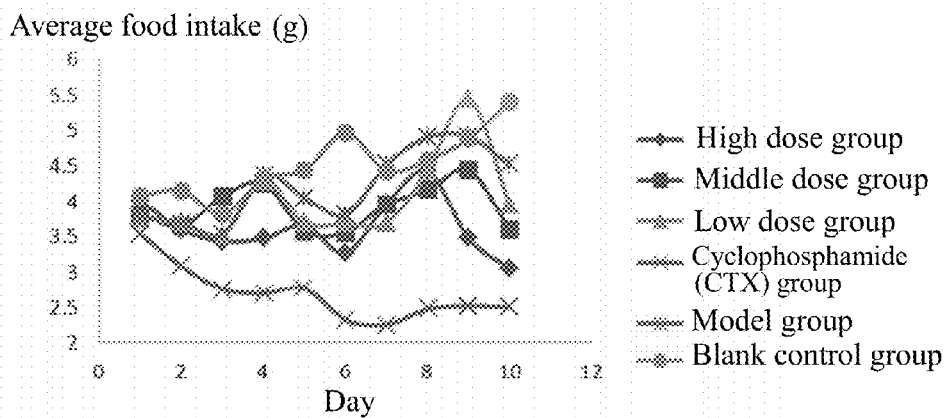
FIG. 12 shows an average food intake of mice during treatment in antitumor experiment of C310-6 against $H_{22}$ tumor bearing mice.
Figure 13:
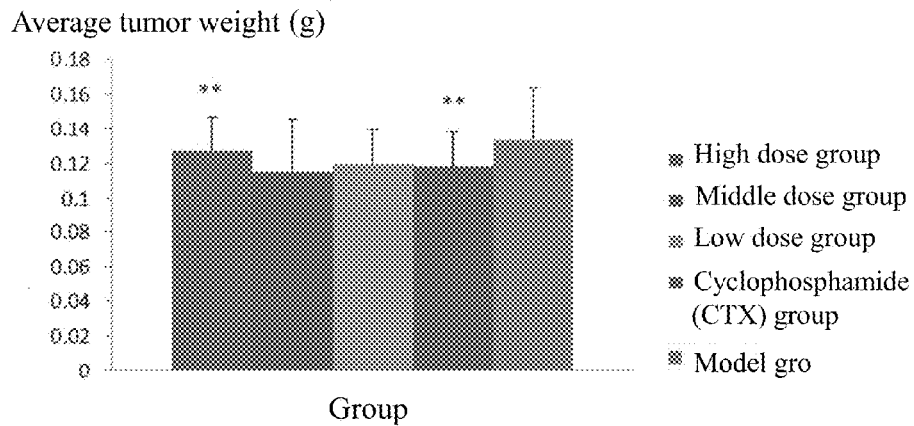
FIG. 13 is a chart showing an average tumor weight (g) of mice in an anti-Lewis tumor experiment of C310-6, in which a high dose group, a middle dose group, a low dose group, a CTX group, and a model group are represented in sequence.
Figure 14:
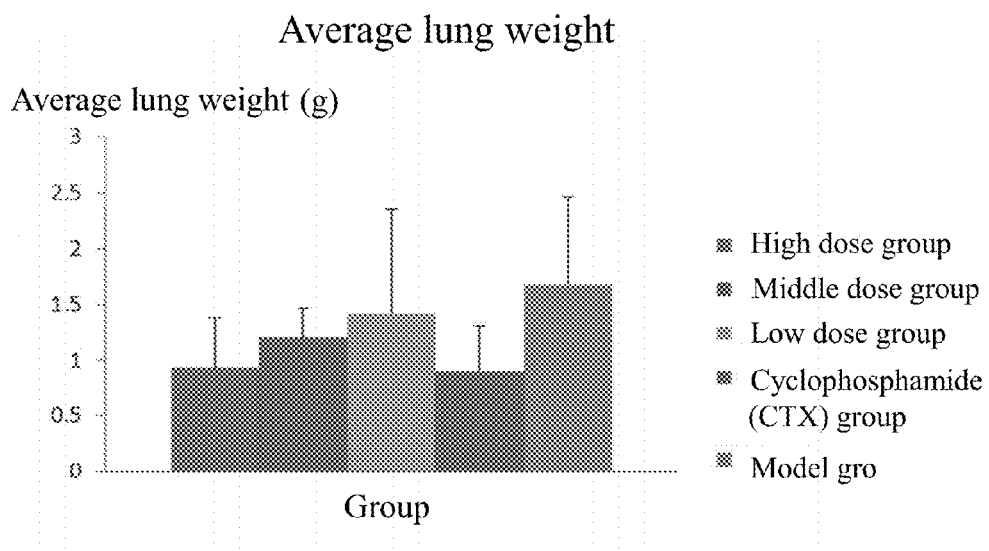
FIG. 14 is a chart showing an average lung weight (g) of mice in an anti-Lewis tumor experiment of C310-6, in which a high dose group, a middle dose group, a low dose group, a CTX group, and a model group are represented in sequence.
Figure 15:
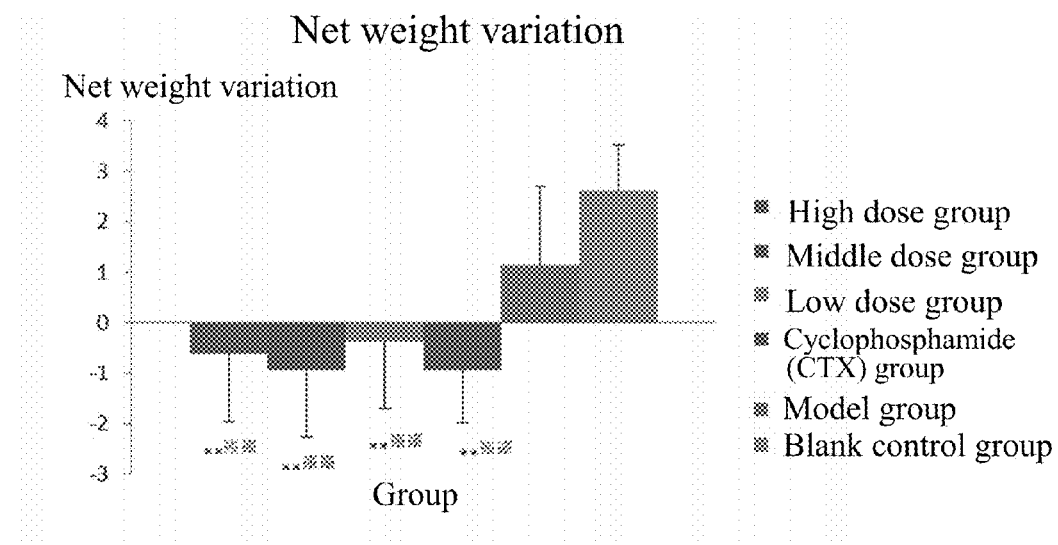
FIG. 15 is a chart showing an average variation of net weight (g) of mice in an anti-Lewis tumor experiment of C310-6, in which a high dose group, a middle dose group, a low dose group, a CTX group, and a model group are represented in sequence.
Figure 16:
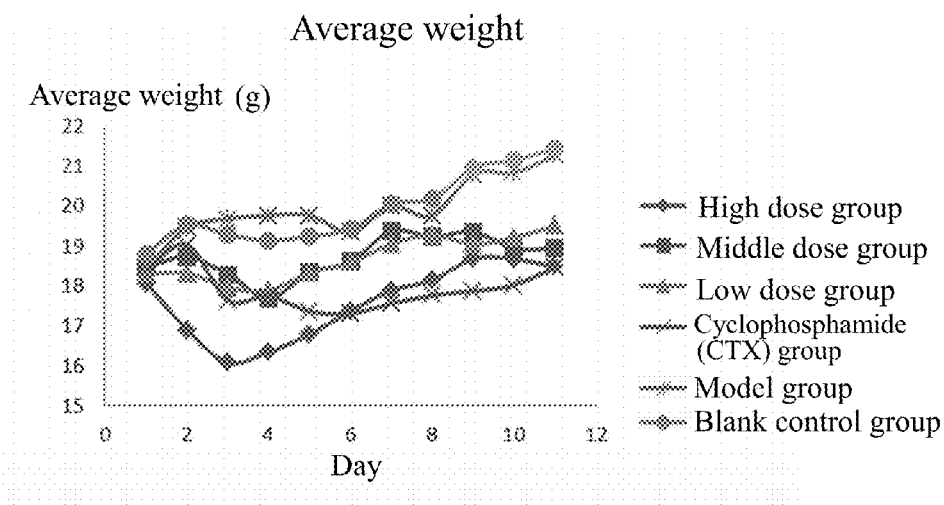
FIG. 16 an average weight variation of mice during treatment in in an anti-Lewis tumor experiment of C310-6.
Figure 17:
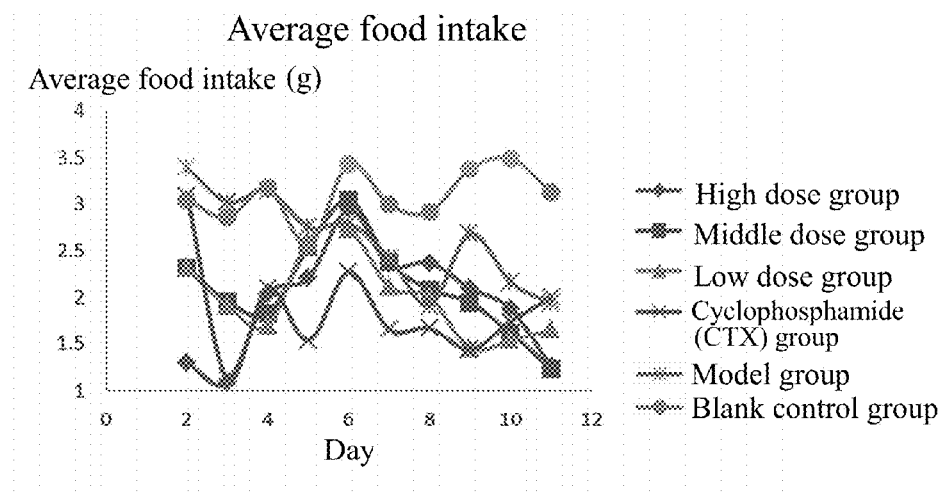
FIG. 17 shows an average food intake of mice during treatment in an anti-Lewis tumor experiment of C310-6.

Real-time data (48 hrs) are shown in FIG. 7 demonstrating growth of the human lung cancer cells A549 inhibited by C310-6 compound of different concentrations.

(super clean bench). The tumors were cut into small piece and transferred to a tissue homogenizer, the normal saline was added with a volume ratio of the tumor piece to the normal saline being 1:3, a resulting homogenate was put into a 50 mL sterile centrifuge tube. 0.2 mL of the homogenate was inoculated to right axilla of each C57BL/6 mouse by 1 mL syringe. The tumor cell suspension was prepared in the sterile environment (the super clean bench), and the serial operations from separation of the abdominal dropsy of the tumor to the tumor inoculation were accomplished in 60 min 2. Preparation of Drugs Oral agent of C310-6: a certain weight of C310-6 sample was placed in a mortar, and Tween-80 having a volume of 2% of a certain volume of a solvent was added and fully ground. Thereafter, the normal saline was added and fully stirred to form a solution. Solutions having a concentration of the C310-6 sample of 24 mg/mL, 8 mg/mL, and 2.7 mg/mL were prepared.

Oral agent of CTX: CTX pill was removed from a film and a certain amount of the pill was placed in a mortar. A certain volume of normal saline was added, fully ground, and mixed to prepare a solution having a concentration of CTX to be 3.4 mg/mL.

2. Grouping and Administration 60 experimental mice were divided into 6 groups with each group having 10 mice, a half of the mice being female and another half of the mice being male. The groups are specifically as follows: 1) group administered with a low dose of C310-6 (27 mg/kg), 2) group administered with middle dose of C310-6 (80 mg/kg), 3) group administered with high dose of C310-6 (240 mg/kg), 4) group administered with CTX, 5) model group, and 6) blank control group. The above groups, except the model group and the blank control group, are administered with 0.3 mL of the drugs once a day after the injection of the tumor suspension, and the administration was lasted for 10 days. The model group and the blank control group are administered orally with equal volume of aqua solutions containing 2 v. % of Tween-80 for 10 days.

4. Observation Indicators 4.1 General Condition

The weight and food intake of the mice were weighed and recorded every day, and a net weight of each mouse after tumor removal was calculated at the last time.

4.2 Tumor Weight and Tumor Inhibition Rate

The right axilla of each mouse was observed every day, and the tumor tissue was separated 24 hrs after the last administration of the drug. The separated tumor tissue was weighed, and the inhibition rate on the tumor growth was calculated according to the following equation:

$$\text{Tumor inhibition rate} = \frac{\text{tumor weight of administration group} - \text{tumor weight of model group}}{\text{tumor weight of model group} \times 100\%}$$

4.3 Liver Tissue Weight and Transmission Rate of Live Cancer

The liver tissue was collected and weighed 24 hrs after the last drug administration, variation of the liver tissue was observed, and mice having liver cancer transmission phenomenon were calculated.

5. Data Statistics

Data of mice in each group were expressed by and were processed by SPSS software, each group was examined by one-way ANOVA.

6. Experimental Results

It is known from Table 7 and FIGS. 8-12 that the group administered with 240 mg/kg of C310-6 is significantly different ($P<0.05$) from the $H_{22}$ model group at the $10^{th}$ day from the drug administration, and the liver cancer inhibition rate is relatively high (>40%) in groups with the administration doses of 240 mg/kg and 80 mg/kg. The group administered with CTX is significantly different ($P<0.05$) from the model group, and is not significantly different from the groups administered with the 80 mg/kg and 240 mg/kg of C310-6.

In the aspect of the liver weight, the group administered with 80 mg/kg of C310-6 is very significantly different ($P<0.01$) from the group administered with CTX, and the group administered with 27 mg/kg of C310-6 is significantly different ($P<0.05$) from the group administered with CTX, and the group administered with CTX is very significantly different ($P<0.01$) from the model group.

In the aspect of the net weight variation, the weight increases of all the groups administered with drugs are relatively small. The group administered with the 240 mg/kg of C310-6 is significantly different ($P<0.05$) from the model group and the blank control group; and the group administered with CTX is very significantly different ($P<0.01$) from the model group and the blank control group.

Cancer cells transmission phenomenon didn't happen in any group of mice.

During the administration, weights of the mice in each group administered with C310-6 represent fluctuation increase and then remain stable. The group administered with CTX keeps at the relatively low weight state. While the model group and the blank control group have larger weight increase than other groups.

During the drug administration, the average food intake of mice in each group administered with C310-6 is stable in a previous period of the administration and in the later period, the average food intake is inversely proportional to the administration dose of the drug. The food intake of the group administered with CTX keeps at a relatively low level. The food intake of the blank control group and the model group always remains at the relatively high level.

TABLE 7

Results of anti-liver cancer experiment ($\bar{x} \pm s$)

| | | | | index | | | | |
|---|---|---|---|---|---|---|---|---|
| Group | Dose (mg/kg) | Animal number | Tumor weight (g) | Tumor inhibition rate (%) | Liver weight (g) | Net weight variation (g) | Survival rate (%) | Liver transfer rate (%) |
| High dose group | 240 | 10 | 0.19 ± 0.18* | 64.4 | 1.57 ± 0.30 | 5.70 ± 4.05*✕∘∘ | 100 | 0 |

TABLE 7-continued

Results of anti-liver cancer experiment ($\bar{x} \pm s$)

| Group | Dose (mg/kg) | Animal number | Tumor weight (g) | Tumor inhibition rate (%) | Liver weight (g) | Net weight variation (g) | Survival rate (%) | Liver transfer rate (%) |
|---|---|---|---|---|---|---|---|---|
| Middle dose group | 80 | 10 | 0.32 ± 0.43 | 41.1 | 1.87 ± 0.52oo | 7.78 ± 3.72oo | 100 | 0 |
| Low dose group | 27 | 10 | 0.42 ± 0.60 | 23.4 | 1.67 ± 0.53o | 6.92 ± 2.65oo | 100 | 0 |
| CTX group | 20 | 10 | 0.25 ± 0.21* | 52.9 | 1.26 ± 0.22** | 1.73 ± 2.73**XX | 100 | 0 |
| Model group | — | 10 | 0.55 ± 0.57 | — | 1.76 ± 0.38 | 9.45 ± 4.00 | 100 | 0 |
| Blank control group | — | 10 | — | — | — | 9.24 ± 4.03 | 100 | — |

Note:
compared with the model group:
**$P < 0.01$, and *$P < 0.05$;
compared with the blank control group: XX$P < 0.01$, and X$P < 0.05$; and
compared with the CTX group: oo$P < 0.01$, and o$P < 0.05$.

In summary, it is assumed that when the mice is administered with C310-6 with the dose of 80 mg/kg for 10 days, C310-6 has significant efficacy (tumor inhibition rate of 41.1%) on the $H_{22}$ liver cancer model, and the efficacy of 310-6 has no obvious difference with that of the CTX. The C310-6 may have the efficacy of preventing hepatomegaly similarly to the CTX. However, the net weight variation (weight after tumor removal compared with the original weight) is relatively small, thus, similar to the CTX, C310-6 may have inhibition effect on the organism weight and the food intake thereof to a certain degree, and the inhibition effect may be positively proportional to the administration amount. When the administration dose is 240 mg/kg, the tumor inhibition rate (64.4%) is even better than that of the CTX (52.9%). In addition, the average tumor weight of the model group is relatively small (<1 g), which may affect the final judgment to a certain degree.

Example 6

Anti-Lewis Tumor Experiment of C310-6

The purpose of the experiment was adopting the Lewis tumor bearing mouse model to observe the antitumor effect of C310-6.

1. Construction of Lewis Lung Cancer Bearing Mouse

Tumor bearing mouse inoculated with the tumor for 8-13 days and in good condition was killed by dislocation. Body surface of the mouse was disinfected by alcohol. The tumors were separated from the mouse and placed in sterile petri dish containing normal saline in a sterile environment (super clean bench). The tumors were cut into small piece and transferred to a tissue homogenizer, the normal saline was added with a volume ratio of the tumor piece to the normal saline being 1:3, a resulting homogenate was put into a 50 mL sterile centrifuge tube. 0.2 mL of the homogenate was inoculated to right axilla of each KM mouse by 1 mL syringe. The tumor cell suspension was prepared in the sterile environment (the super clean bench), and the serial operations from the tumor separation to the tumor inoculation were accomplished in 60 min 2. Preparation of Drugs Oral agent of C310-6: a certain weight of C310-6 sample was placed in a mortar, and Tween-80 having a volume of 2% of a certain volume of a solvent was added and fully ground. Thereafter, the normal saline was added and fully stirred to form a solution. Solutions having a concentration of the C310-6 sample of 24 mg/mL, 8 mg/mL, and 2.7 mg/mL were prepared.

Oral agent of CTX: CTX pill was removed from a film and a certain amount of the pill was placed in a mortar. A certain volume of normal saline was added, fully ground, and mixed to prepare a solution having a concentration of CTX to be 3.4 mg/mL.

2. Grouping and Administration 60 experimental mice were divided into 6 groups with each group having 10 mice, a half of the mice being female and another half of the mice being male. The groups are specifically as follows: 1) group administered with a low dose of C310-6 (27 mg/kg), 2) group administered with middle dose of C310-6 (80 mg/kg), 3) group administered with high dose of C310-6 (240 mg/kg), 4) group administered with CTX, 5) model group, and 6) blank control group. The above groups, except the model group and the blank control group, are administered with 0.2 mL of the drugs once a day after the injection of the tumor suspension, and the administration was lasted for 10 days. The model group and the blank control group are administered orally with equal volume of aqua solutions containing 2 v. % of Tween-80 for 10 days.

4. Observation Indicators 4.1 General Condition

The weight and food intake of the mice were weighed and recorded every day, and a net weight of each mouse after tumor removal was calculated at the last time.

4.2 Tumor Weight and Tumor Inhibition Rate

The right axilla of each mouse was observed every day, and the tumor tissue was separated 24 hrs after the last administration of the drug. The separated tumor tissue was weighed, and the inhibition rate on the tumor growth was calculated according to the following equation:

$$\text{Tumor inhibition rate} = \frac{\text{tumor weight of administration group} - \text{tumor weight of model group}}{\text{tumor weight of model group} \times 100\%}$$

4.3 Lung Tissue Weight and Transmission Rate of Lung Cancer

The lung tissue was collected and weighed 24 hrs after the last drug administration, variation of the lung tissue was observed, and mice having lung cancer transmission phenomenon were calculated.

5. Data Statistics

Data of mice in each group were expressed by corresponding data and were processed by SPSS software, each group was examined by one-way ANOVA.

6. Experimental Results

It is known from Table 8 and FIGS. 13-17 that the group administered with 240 mg/kg of C310-6 is very significantly different (P<0.01) from the Lewis lung cancer model group at the $10^{th}$ day from the drug administration, and such administration dose of C310-6 has no obvious difference with the CTX group.

In the aspect of the lung cancer transmission, the lung cancer transmission phenomenon occurs in 20%-50% of mice in each group, which has non statistical significance.

In the aspect of the net weight variation, those groups administered with C310-6 and CTX respectively represent decrease in the weight, and each of these group has significant difference (P<0.01) with the model group and the blank control group.

During the administration, weights of the mice in each group administered with C310-6 represent decrease, fluctuation increase, and continued with a stable state. The group administered with CTX represents a descending trend first and then remaining in low weight state. While both the model group and the blank control group represents fluctuation increase and then remaining in a certain weight level.

During the drug administration, the average food intake of mice in each group administered with C310-6 is relatively high in a middle period and is relatively low in both the previous and the later periods. The food intake of the group administered with CTX keeps at a relatively low level. The food intake of the blank control group keeps at a relatively high level, while the model group represents a gradual descending trend of the food intake.

In summary, it is assumed that when the mice is administered with C310-6 with the dose of 240 mg/kg for 10 days, C310-6 has relatively good efficacy in the Lewis lung cancer model, and organisms administered with C310-6 may represents weight decrease, but the adverse effect resulted from the C310-6 administration is smaller than that of the CTX.

Thus, (3α,9β,10α,13α,14β,17α,20S,22E)-ergosta-5,7,22-trien-3-ol and/or the crystals thereof have been proven to possess antitumor activity. In the level of activity of cells in vitro, the activity of the compound is measured by the real-time cell-analyzer and the MTT method, and experiment results show that the compound has obvious inhibition on liver cancer and lung cancer cells. In the level of the integrate animals, the experiment results show that the compound has obvious inhibition on the liver cancer and lung cancer. Thus, the compound and the pharmaceutical excipient can be prepared into antitumor drugs suitable for clinical use.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A crystal, being acquired by crystallization of (3α,9β,10α,13α,14β,17α,20S,22E)-Ergosta-5,7,22-trien-3-ol having a chemical structure represented by Formula (I),

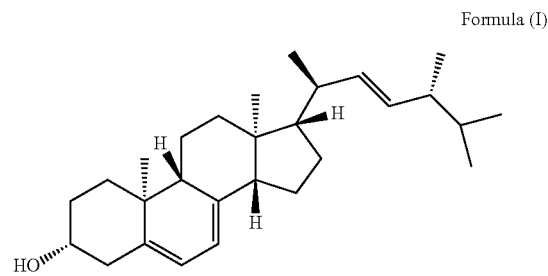 [SMILES: CC(C)[C@@H](C)/C=C/[C@H](C)[C@@H]1CC[C@@H]2C3=CC=C4C[C@H](O)CC[C@@]4(C)[C@@H]3CC[C@]21C]

Formula (I)

TABLE 8

Results of anti-lung cancer experiment ($\bar{x} \pm s$)

| Group | Dose (mg/kg) | Animal number | Tumor weight (g) | Tumor inhibition rate(%) | Liver weight (g) | Net weight variation (g) | Survival rate (%) | Lung cancer transmission rate (%) |
|---|---|---|---|---|---|---|---|---|
| High dose group | 240 | 10 | 0.93 ± 0.45** | 44.59 | 0.13 ± 0.02 | −0.61 ± 1.36**XX | 100 | 30 |
| Middle dose group | 80 | 10 | 1.21 ± 0.26 | 28.39 | 0.12 ± 0.03 | −0.95 ± 1.30**XX | 100 | 50 |
| Low dose group | 27 | 10 | 1.42 ± 0.94 | 15.76 | 0.12 ± 0.02 | −0.36 ± 1.33**XX | 100 | 40 |
| CTX group | 20 | 10 | 0.90 ± 0.39** | 46.29 | 0.12 ± 0.02 | −0.94 ± 1.03**XX | 100 | 20 |
| Model group | — | 10 | 1.68 ± 0.78 | — | 0.13 ± 0.03 | 1.16 ± 1.55 | 100 | 50 |
| Blank control group | — | 10 | — | — | — | 2.63 ± 0.88 | 100 | — |

Note:
compared with the model group: **P < 0.01, and *P < 0.05;
compared with the blank control group: XXP < 0.01, and XP < 0.05.

wherein
a single crystal type of the crystal belongs to a monoclinic crystal system, crystal axes thereof are a=9.848(2), b=7.5529(15), and c=35.074(7); and
angles between crystal faces are α=90°, β=95.62(3)°, and λ=90°.

2. The crystal of claim 1, wherein in a chemical structure of the compound represented by Formula (II),

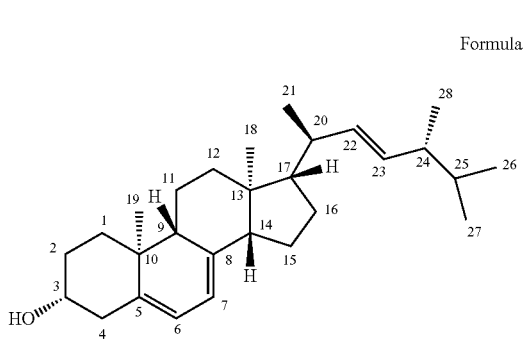

Formula (II)

chiral carbons of C-3, C-9, C-10, and C-24 are in an R configuration, and the
chiral carbons of C-13, C-14, C-17, and C-20 are in an S configuration.

3. A pharmaceutical composition comprising a compound and/or a crystal of (3α,9β,10α,13α,14β,17α,20S,22E)-Ergosta-5,7,22-trien-3-ol having a chemical structure represented by Formula (I), and a pharmaceutically accepted excipient,

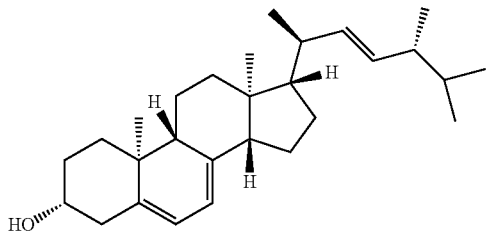

Formula (I)

wherein
the crystal is acquired by crystallization of the compound;
a single crystal type of the crystal belongs to a monoclinic crystal system, crystal axes thereof are a=9.848(2), b=7.5529(15), and c=35.074(7); and
angles between crystal faces are α=90°, β=95.62(3)°, and λ=90°.

* * * * *